US007407658B2

(12) United States Patent
Kaslow et al.

(10) Patent No.: US 7,407,658 B2
(45) Date of Patent: Aug. 5, 2008

(54) **VACCINES FOR BLOCKING TRANSMISSION OF *PLASMODIUM VIVAX***

(75) Inventors: David C. Kaslow, Wayne, PA (US); Takafumi Tsuboi, Ehime (JP); Motomi Torii, Ehime (JP)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/611,779

(22) Filed: Dec. 15, 2006

(65) Prior Publication Data

US 2007/0110772 A1    May 17, 2007

Related U.S. Application Data

(63) Continuation of application No. 09/554,960, filed as application No. PCT/US98/25742 on Dec. 4, 1998, now Pat. No. 7,192,934.

(60) Provisional application No. 60/067,596, filed on Dec. 5, 1997, provisional application No. 60/045,283, filed on May 1, 1997.

(51) Int. Cl.
*A61K 39/00* (2006.01)
*A61K 39/015* (2006.01)

(52) U.S. Cl. .................. 424/185.1; 424/272.1

(58) Field of Classification Search ............. 424/185.1, 424/272.1
See application file for complete search history.

(56) References Cited

FOREIGN PATENT DOCUMENTS

| WO | WO 89/10936 A1 | 11/1989 |
|---|---|---|
| WO | WO 94/01552 A1 | 1/1994 |
| WO | WO 94/28930 A1 | 12/1994 |
| WO | WO 95/08631 A2 | 3/1995 |
| WO | WO 98/14472 A1 | 4/1998 |

OTHER PUBLICATIONS

Duffy et al, A novel malaria protein, Pfs28, and Pfs25 are genetically linked and synergistic as falciparum malaria transmission-blocking vaccines, 1997, Infect Immun, vol. 65:1109-13.*

Kaslow et al, Production, Purification and Immunogenicity of a Malaria Transmission-Blocking Vaccine Candidate: TBV25H Expressed in Yeast and Purified Using Nickel-NTA Agarose. 1994, Natur Biotechnology, vol. 12:494-9.*

Miller et al, New gene for 25 kDa surface antigen of plasmodium falciparum—in sexual development stages, useful in transmission-blocking malaria vaccine. 1990, SCORE result.*

Hisaeda, H., et al., "Antibodies to Malaria Vaccine Candidates Pvs25 and Pvs28 Completely Block the Ability of *Plasmodium vivax* To Infect Mosquitoes," *Infection and Immunity*, vol. 68, No. 12, pp. 6618-6603 (Dec. 2000).

Kofta, W., et al., "c-DNA vaccination against parasitic infections: advantages and disadvantages," *Veterinary Parasitology*, vol. 100, pp. 3-12 (2001).

Kongkasuriyachai, D., et al., "Potent immunogenicity of DNA vaccines encoding *Plasmodium vivax* transmission-blocking vaccine candidates Pvs25 and Pvs28—evaluation of homologous and heterologous antigen-delivery prime-boost strategy," *Vaccine*, vol. 22, pp. 3205-3213 (2004).

McCluskie, M., et al., "Route and Method of Delivery of DNA Vaccine Influence Immune Responses in Mice and Non-Human Primates," Molecular Medicine, vol. 5, pp. 287-300 (1999).

Mendis, K. et al., "Immune modulation of parasite transmission in *Plasmodium vivax* malaria: Anti-gamete antibodies can both block and enhance transmission"; *Molecular Strategies of Parasitic Invasion*; pp. 417-426, 1987. Alan R. Liss, Inc.

Premawansa, S. et al., "Target antigens of transmission blocking immunity of *Plasmodium vivax* malaria: Characterization and polymorphism in natural parasite isolates"; *J. Immunol*. vol. 144 (11), pp. 4376-4383 (Jun. 1, 1990).

Snewin, V. et al., "Transmission blocking immunity in *Plasmodium vivax* malaria: Antibodies raised against a peptide block parasite development in the mosquito vector"; *J. Exp. Med.*, vol. 181, pp. 357-362 (Jan. 1995).

Tsuboi, T., et al., "Sequence Polymorphism in Two Novel *Plasmodium vivax* Ookinete Surface Proteins, Pvs25 and Pvs28, That Are Malaria Transmission-blocking Vaccine Candidates," *Molecular Medicine*, vol. 4, pp. 772-782 (1998).

* cited by examiner

*Primary Examiner*—Mark Navarro
(74) *Attorney, Agent, or Firm*—Townsend and Townsend and Crew LLP

(57) ABSTRACT

The present invention relates novel methods and compositions for blocking transmission of *Plasmodium vivax* which cause malaria. In particular, Pvs25 and Pvs28 polypeptides, variants, including deglycosylated forms, and fusion proteins thereof, are disclosed which, when administered to a susceptible organism, induce an immune response against a 25 kD and 28 kD protein, respectively, on the surface of *Plasmodium vivax* zygotes and ookinetes. This immune response in the susceptible organism can block transmission of malaria.

17 Claims, 7 Drawing Sheets

FIGURE 1

Pvs28 Nucleotide Sequence

```
       tccactctcttcttccacacttatcttgttcccc
  40   ccattcggccaccaactgcattatacaaaaacgactcccc
  80   ctttgagataaacaccaactgagctgattccccctcccc
 120   actttgcgcctccccttgttcaaaatgaatacctacca
 160   cagcttgcttccttctggccatcgtgcttactgttaag
 200   cacacctcgcaaaggtcaccgcggagacccaatgcaaaa
 240   atggctatgtagtccaaatgagcaatcattttgaatgcaa
 280   atgcaacgacggggttttgttatgcaaatgaaaacacttgc
 320   gaggaaaaacgcgattgcacaaatccacaaaatgtaaata
 360   aaaactgtggagactacgctgtgtgcaaacaccagaat
 400   gaatgatgaggaaagagcattacgatgcggctgcatatta
 440   gggtacaccgtaatgaatgaggtgtgtactccaaataaat
 480   gtaacggcgttttgtgtgaacagcaccatgctctctgtaatata
 520   tcccgctaatgtgaacagcaccatgctctctgtaatata
 560   ggaaccacattggatgaatctaaaaatgtggnaagccag
 600   gaaaaactgaatgcacgttgaagtgtaaggcaaacgaaga
 640   atgtaaaagagactcagaattattacaagtgcgttgcgaag
 680   ggaagcggcggagaaggcagcggtggagaaggcagcggcg
 720   gagagggcagcggcggagaaggcagcggcggagaggggcag
 760   cggtggagacacaggagcagcagcttacagtctcatgaacgga
 800   tctgcagtaatcagcatactacttgtattcgcctctca
 840   tgatgtcattagtgtagacgattctacacacacacaaa
 880   catacacaaggggagaagcgtctcacagagtcagttcaag
 920   tcatacgcacaaaaaggaaagtacatccagctggtgaaa
 960   gagcatttatgtgtgcagttatcctgggagaagcaccct
1000   ccaccagttgcgttgctgttaccttaaaacttagtgca
1040   cccatatcgaatttgacttgctcgc                    1066
```

FIGURE 2

Pvs28 Amino Acid Sequence

N-terminal-

MNTYHSLLFLLAIVLTVKHTFAKVTAEFQCKNGYVVQMSNHFECKCNDGFVMANENTCEEKRDCTNPQNVNKNCGDYAVCA
NTRMNDEERALRCGCILGYTVMNEVCTPNKCNGVLCGKGKCILDPANVNSTMCSCNIGTTLDESKKCGKPGKTECTLKCCKANE
ECKETQNYYKCVAKGSGGEGSGGEGSGGEGSGGEGSGGDTGAAYSLMNGSAVISILLVFAFFMMSLV

-C-terminal

FIGURE 3

Pvs25 Nucleotide Sequence

5'-
CTGACTTTCGTTTCACAGCACTGATTTTTTGTTCGACCGGCTCAATTCGC
CACTTGCCATTTCGATTGTTTGCTTGTTTGCTTTTTGCTTTTGCTTATTCGCCC
GTTTTCCGCTTGCCCGTTGCGCCCGTTCCACAACGCGCCCGCTGCAAAGGT
TGCCCACCACCGACCACAAAAACTTATTCACCACCATCCGAGCGGAAAGG
AACGCGCCACTGTGCTGCCTACCTCCCCGAATAACAACTCCACTTAGC
CAAAATGAACTCCTACTACAGCCCTCTCGTTTTTTCCTCGTCCAAATTG
CGCTAAAGTATAGCAAGGCAGCCGTCACGTAGACACCATATGCAAAAAT
GGACAGCTGGTTCAAATGAGTAACCACTTTAAGTGTATGTGTAACGAAGG
GCTGGTGCACCTTTCCGAAAATACATGCGGGGAATTTGGCCAGTGTATAGAAAAC
AAGAAACCCTAGGCAAAGCATGCGGGGAATTTGGCCAGTGTATAGAAAAC
CCAGACCACCAGGCACAGGTAAACACTGTGTGCTTGATGTATGTCAATACAAAATT
CACTTTGAAGGAAGACACTGTGTGCTTGATGTATGTCAATACAAAATT
GTGGAGAAAGTGGCGAATGCATTGTTGAGTACCTCTCGGAAATCCAAAGT
GCAGGTTGCTCATGTGCTATTGGCAAAGTCCCCAATCCAGAAGATGAGAA
AAAATGTACCAAAACGGGAGAAACTGCTTGTCAATTGAAATGTAACACAG
ATAATGAAGTCTGCAAAAATGTTGAAGGAGTTTACAAGTGCCAGTGTATG
GAAGGCTTTACGTTCGACAAAGAGAAAAATGTATGCCTTTCCTATTCTGT
ATTTAACATCCTAAACTACTCCCTCTCTTTATCATCCTGCTTGTCCTTT
CGTACGTCATATAAGTGCGAAACTTGCGCAGCTAAGCAGGCAAATTTTT
TAAGTAAAATACTTTCTTTACTGAACTTACCGACTTGTGATGT
-3'

FIGURE 4

Pvs25 Amino Acid Sequence

N-terminal-
MNSYYSLFVFFLVQIALKYSKAAVTVDTICKNGQLVQMSNHFKCMCNEGL
VHLSENTCEEKNECKKETLGKACGEFGQCIENPDPAQVNMYKCGCIEGYT
LKEDTCVLDVCQYKNCGESGECIVEYLSEIQSAGCSCAIGKVPNPEDEKK
CTKTGETACQLKCNTDNEVCKNVEGVYKCQCMEGFTFDKEKNVCLSYSVF
NILNYSLFFIILVLSYVI
-C-terminal

FIGURE 5

Pvs25-Pvs28 Fusion Protein Amino Acid Sequence

N-terminal-

AVTVDTICKNGQLVQMSNHFKCMCNEGLVHLSENTCEEKNECKKETLGKACGEFGQCIENPDPAQVNMYKCGCIEGYTLKED
TCVLDVCQYKNCGESGECIVEYLSEIQSAGCSCAIGKVPNPEDEKKCTKTGETACQLKCNTDNEVCKNVEGVYKCQCMEGFTF
DKEKNVCLS GGGPGGG AKVTAETQCKNGYVVQMSNHFECKCNDGFVMANENTCEEKRDCTNPQNVNKNCGDYAVCANT
RMNDEERALRCGCILGYTVMNEVCTPNKCNGVLCGKGKCILDPANVNSTMCSCNIGTTLDESKKCCGKPGKTECTLKCKANEEC
KETQNYYKCVAKGSGGEGSGGEGSGGEGSGGDTGAAYSLMN

-C-terminal

GGGPGGG linker sequence underlined.

Figure 6

Constructs and recombinant protein of Pvs25 and Pvs28

Pvs25

EAEASAVTVDTICKNGQLVQMSNHFKCMCNEGLVHLSENTCEEKNECKKET 50
LGKACGEFGQCIENPDPAQVNMYKCGCIEGYTLKEDTCVLDVCQYKNCGES 100
GECIVEYLSEIQSAGCSCAIGKVPEPEDEKKCTKTGETACQLKCNTDNEVC 150
KNVEGVYKCQCMEGFTFCKEKNVCLGPHHHHHH 186 (SEQ ID NO:16)

Pvs28

EAEASKVTAETQCKNGYVVQMSNHFECKCNDGFVLANENTCEEKRDCTNP 50
QNVNKNCGDYAVCANTRMNEERALRCGCILGYTVMNEVCTPYKCNGVLC 100
GKGKCILDPANVNSTMCSCNIGSTLDESKKCGKPGKTECTLKCCKANEECK 150
ETQNYYKCVAKGSSGGEGSGGEGSSGGEGSSGGEGSGGDTGAAYSGPH 200
HHHHH 205 (SEQ ID NO:17)

Pvs28Q130

EAEASKVTAETQCKNGYVVQMSNHFECKCNDGFVLANENTCEEKRDCTNP 50
QNVNKNCGDYAVCANTRMNEERALRCGCILGYTVMNEVCTPYKCNGVLC 100
GKGKCILDPANVQSTMCSCNIGSTLDESKKCGKPGKTECTLKCCKANEECK 150
ETQNYYKCVAKGSSGGEGSGGEGSSGGEGSSGGEGSGGDTGAAYSGPH 200
HHHHH 205 (SEQ ID NO:18)

Pvs28NCR

EAEASKVTAETQCKNGYVVQMSNHFECKCNDGFVLANENTCEEKRDCTNP 50
QNVNKNCGDYAVCANTRMNEERALRCGCILGYTVMNEVCTPYKCNGVLC 100
GKGKCILDPANVNSTMCSCNIGSTLDESKKCGKPGKTECTLKCCKANEECK 150
ETQNYYKCVAKGPHHHHHH 169 (SEQ ID NO:19)

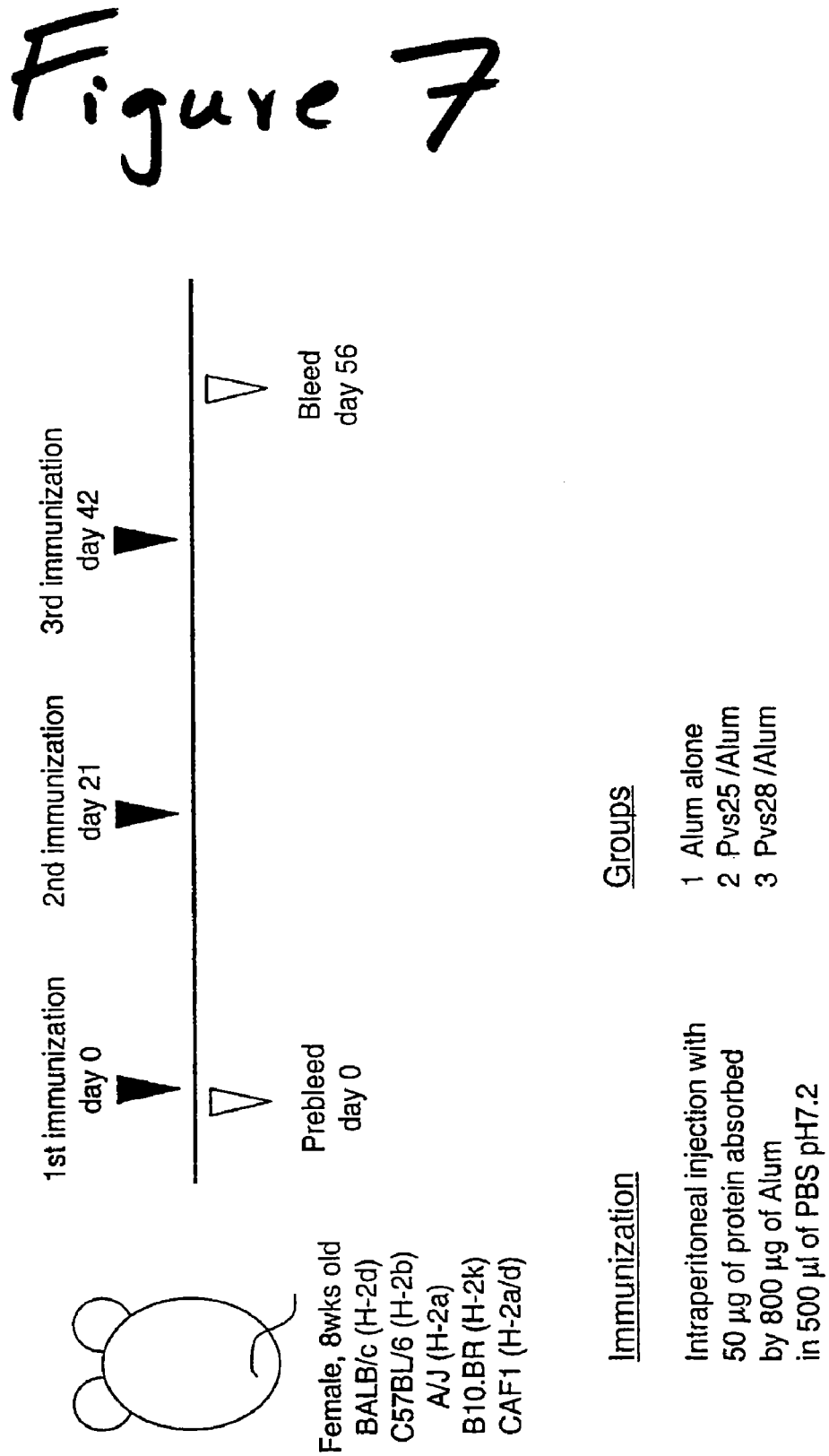

VACCINES FOR BLOCKING TRANSMISSION OF PLASMODIUM VIVAX

CROSS-REFERENCES TO RELATED APPLICATIONS

The present application is a Continuation of U.S. Ser. No. 09/554,960, filed Feb. 12, 2003, which is a National Stage Entry of PCT/US98/25742, filed Dec. 4, 1998, which claims the benefit of U.S. Provisional Application Ser. No. 60/067,596, filed Dec. 5, 1997; and U.S. Provisional Application Ser. No. 60/045,283, filed May 1, 1997. The aforementioned applications are explicitly incorporated herein by reference in their entirety and for all purposes.

BACKGROUND OF THE INVENTION

Malaria continues to exact a heavy toll from mankind. Between 200 million to 400 million people are infected by *Plasmodium falciparum* and *Plasmodium vivax*, the deadliest of the malarial protozoans, each year. One to four million of these people die.

*Plasmodium vivax* is probably the most prevalent form of malaria in humans. It is rare in most of Africa because many Africans are Duffy blood group negative and *P. vivax* requires the Duffy blood group for invasion. Although *P. vivax* does not often lead to death, it causes incomprehensible suffering and debilitation in hundreds of millions of humans every year.

The life cycle of the malaria parasite is complex. Infection in man begins when young malarial parasites or "sporozoites" are injected into the bloodstream of a human by a mosquito. After injection the parasite localizes in liver cells. Approximately one week after injection, the parasites or "merozoites" are released into the bloodstream to begin the "erythrocytic" phase. Each parasite enters a red blood cell in order to grow and develop. When the merozoite matures in the red blood cell, it is known as a trophozoite and, when fully developed, as a schizont. A schizont is the stage when nuclear division occurs to form individual merozoites which are released to invade other red cells. After several schizogonic cycles, some parasites, instead of becoming schizonts through asexual reproduction, develop into large uninucleate parasites. These parasites undergo sexual development.

Sexual development of the malaria parasites involves the female or "macrogametocyte" and the male parasite or "microgametocyte." These gametocytes do not undergo any further development in man. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs with the fusion of the microgamete and a macrogamete. The fertilized parasite, which is known as a zygote, then develops into an "ookinete." The ookinete penetrates the midgut wall of the mosquito and develops into an oocyst, within which many small sporozoites form. When the oocyst ruptures, the sporozoites migrate to the salivary gland of the mosquito via the hemolymph. Once in the saliva of the mosquito, the parasite can be injected into a host, repeating the life cycle.

Malaria vaccines are needed against different stages in the parasite's life cycle, including the sporozoite, asexual erythrocyte, and sexual stages. Each vaccine against a particular life cycle stage increases the opportunity to control malaria in the many diverse settings in which the disease occurs. For example, sporozoite vaccines would fight infection immediately after injection of the parasite into the host by the mosquito. First generation vaccines of this type have been tested in humans. Asexual erythrocytic stage vaccines would be useful in reducing the severity of the disease. Multiple candidate antigens for this stage have been cloned and tested in animals and in humans.

However, as drug-resistant parasite strains render chemoprophylaxis increasingly ineffective, a great need exists for a transmission-blocking vaccine. Such a vaccine would block the portion of the parasite's life cycle that takes place in the mosquito or other arthropod vector, thus preventing even the initial infection of humans. Several surface antigens serially appear on the parasite as it develops from gametocyte to gamete to zygote to ookinete within the arthropod midgut (Rener et al., J. Exp. Med. 158: 976-981, 1983; Vermeulen et al., J. Exp. Med. 162: 1460-1476, 1985). Several of these antigens induce transmission-blocking antibodies.

The present invention fills the need for a means to completely block transmission of malaria parasites. The vaccine of the invention meets the requirements for a vaccine for controlling endemic malaria in developing countries: it induces high, long-lasting antibody titers, and can be produced in large amounts, at the lowest possible cost.

BRIEF SUMMARY OF THE INVENTION

The present invention relates to methods for preventing transmission of malaria, particularly *Plasmodium vivax*. The invention relates to methods for eliciting an immune response against parasites responsible for malaria. These methods comprise administering to a susceptible organism a pharmaceutical composition comprising Pvs28 polypeptides (such as SEQ ID NO:2), including partially or completely deglycosylated Pvs28 polypeptides, Pvs25 polypeptides (such as SEQ ID NO:4), variants thereof, or Pvs25/Pvs28 fusion proteins (such as SEQ ID NO:5), in an amount sufficient induce an immune response against a 25 kD and 28 kD protein, respectively, on the surface of *Plasmodium vivax* zygotes and ookinetes. The immune response in the susceptible organism can block transmission of malaria.

The invention also relates to methods of preventing transmission of malaria comprising administering to a susceptible organism a pharmaceutical composition comprising a recombinant virus or expression cassette encoding a *Plasmodium vivax* polypeptide, including Pvs28 polypeptides (including partially or completely deglycosylated Pvs28 polypeptides), Pvs25 polypeptides, or Pvs25/Pvs28 fusion proteins, in an amount sufficient to block transmission of the disease.

The invention further relates to pharmaceutical compositions comprising a pharmaceutically acceptable carrier and a Pvs28 polypeptide (including partially or completely deglycosylated Pvs28 polypeptides), a Pvs25 polypeptide, or a Pvs25/Pvs28 fusion protein, as described herein.

The invention also relates to isolated nucleic acids comprising nucleotide sequences encoding Pvs28 polypeptides (including partially or completely deglycosylated Pvs28 polypeptides), Pvs25 polypeptides, or Pvs25/Pvs28 fusion proteins. These nucleic acids may be isolated from, for instance, *P. vivax*. The sequences are typically contained in an expression vector for recombinant expression of the proteins. The sequences can also be incorporated into recombinant viruses, vectors or expression cassettes for use as nucleic acid vaccines, including "naked DNA" vaccines, for recombinant expression of the proteins in vivo. In another embodiment, the nucleic acids of the invention comprise a pharmaceutical excipient and are injected into a host, e.g., as "naked" DNA vectors or "expression cassettes" injected into muscle, to express recombinant protein in vivo, to induce transmission blocking antibodies against encoded polypeptides.

The invention also provides a composition comprising an isolated nucleic acid molecule encoding a *Plasmodium vivax* Pvs28 polypeptide lacking at least one N-linked glycosylation site. In alternative embodiments, the nucleic acid encodes a polypeptide comprising a sequence as set forth in SEQ ID NO:2, excepting that the amino acid residue corresponding to residue 130 of SEQ ID NO:2 is not an asparagine residue; and the amino acid residue corresponding to residue 130 of SEQ ID NO:2 is glutamine.

The invention also provides a composition comprising an isolated *Plasmodium vivax* Pvs28 polypeptide lacking at least one N-linked glycosylation site. In alternative embodiments, the polypeptide comprises a sequence as set forth in SEQ ID NO:2, excepting that the amino acid residue corresponding to residue 130 of SEQ ID NO:2 is not an asparagine residue; and, the amino acid residue corresponding to residue 130 of SEQ ID NO:2 is glutamine.

The invention further provides a method of inducing a transmission blocking immune response in a mammal, comprising administering a partially or completely deglycosylated Pvs28 polypeptide, or a nucleic acid encoding such a polypeptide, to a mammal.

Pvs28 (including partially or completely deglycosylated Pvs28) as an immunogenic carrier is provided for by the invention. Pvs28, administered with a second composition, provides a superior antigenic response to the second composition. Thus, the invention relates to an immunogenic composition capable of eliciting an immunogenic response directed to an epitope comprising an isolated Pvs28 and an isolated molecule comprising the epitope. The invention is also directed to methods of eliciting an immunogenic response directed to an epitope comprising administering an isolated Pvs28 and an isolated molecule comprising the epitope. The Pvs28 and the second molecule can be chemically linked or joined together as recombinant fusion proteins.

In one embodiment, the Pvs28-containing fusion protein is a Pvs25-Pvs28 fusion protein. The Pvs28 polypeptide can be designed to be partially or completely deglycosylated, as described herein. The sexual stage malarial proteins Pvs25 and Pvs28, in the form of a Pvs25-Pvs28 fusion protein, will generate transmission-blocking antibodies against both Pvs25 and Pvs28. These fusion proteins have enhanced antigenic properties, as compared to use of either alone as an immunogen.

The invention also provides for Pvs25/Pvs28, Pvs25, partially or completely deglycosylated Pvs28, and Pvs28 fusion proteins, and the nucleic acids encoding such polypeptides, further comprising non-malarial sequences. For example, a Pvs25, Pvs28, or Pvs25/Pvs28 polypeptide of the invention can further comprise epitope tags, enzyme cleavage sequences, leader sequences, sequences which cause the polypeptides to be transported to a particular intracellular organelle, and the like. For example, as discussed below, inclusion of yeast alpha mating pheromone signal sequence in a fusion protein of the invention allows for secretion of the expressed Pvs25 or Pvs28. These fusion proteins can provide for simplified manufacturing of Pvs25-Pvs28 antigens.

In one class of embodiments, the Pvs25-Pvs28 fusion protein includes an N terminal Pvs25 domain and a C terminal Pvs28 domain. This arrangement of Pvs25 and Pvs28 in a fusion protein provides superior antigenic and transmission blocking properties for the fusion protein. In one preferred embodiment, the C terminal Pvs28 domain includes the carboxyl terminal region of Pvs28. Exemplar fusion proteins are provided in the examples set forth herein, and conservative modifications thereof.

Typically, the Pvs25-Pvs28 fusion proteins of the invention include a flexible linker separating the Pvs25 and Pvs28 domains. An exemplar flexible linker is the amino acid sequence GGGPGGG (SEQ ID NO:15).

In one embodiment, the fusion proteins (as Pvs25 and Pvs28) are produced recombinantly. The recombinant proteins of the invention can be expressed, e.g., in vitro, in prokaryotic or in eukaryotic systems. In alternative embodiments, bacterial, yeast, insect, plant, mammalian, or other expression systems can be used.

In another embodiment, a nucleic acid encoding a fusion protein of the invention is optimized for expression in a particular expression system, such as preferred codon usage in bacteria or partial or complete deglycosylation by mutation for yeast expression, thereby facilitating recombinant expression and manufacturing of the polypeptide of the invention. For example, Pvs25 and Pvs28 consist of four epidermal growth factor-like (EGF) domains (similar domains are found in the related Pfs25 and Pfs28 Plasmodium polypeptides). These EGF domains comprise structural domains in the molecules. In alternative embodiments, the immunogen includes one or more domains in a variety of permutations and orientations. As domains may require disulfide bonds to create and maintain structural integrity, alternative embodiments encompass various expression systems that faithfully recreate these disulfide linkages.

In another embodiment, the Pvs25, Pvs28 or Pvs25-Pvs28 fusion protein sequences can be mutated or altered, e.g., using site-specific mutational methodologies. For example, in one embodiment, the Pvs25 and Pvs28 sequences are mutated to eliminate one, several or all potential glycosylation sites. Such mutations can facilitate recombinant expression and manufacturing of the polypeptides of the invention, as in yeast expression systems. The partially or completely deglycosylated Pvs polypeptides of the invention are, in some circumstances, better immunogens, i.e., administration of these forms enhance the antigenicity of the polypeptide. For example, in one embodiment, an amino acid residue at position 130 of Pvs28 is altered to remove a potential glycosylation site.

In other embodiments, the different domains of the immunogenic composition are joined, or linked, together by chemical means. In further embodiments, the domains of the immunogenic compositions are derived from natural sources.

The Pvs25-Pvs28 fusion protein, when administered to a mammal, elicits the production of at least two classes of antibodies: antibodies which specifically bind to Pvs25, and antibodies which specifically bind to Pvs28. In preferred embodiments, the administration of the fusion proteins of the invention elicit a transmission blocking immune response. Immunological enhancers and pharmaceutically acceptable carriers are optionally added to the fusion protein to enhance the immunogenicity of the fusion protein and to facilitate delivery of the fusion protein to a mammal. For example, in alternative embodiments, adjuvants such as alum are added.

Immunogenic compositions comprising the fusion proteins of the invention elicit transmission blocking antibodies in a variety of mammals, including humans and other primates, and mice and other rodents.

Cells expressing the nucleic acids and polypeptide of the invention are a feature of the invention. For example, recombinant cells such as yeast cells can be used to express the Pvs25-Pvs28 fusion protein of the invention. Cell lines containing a nucleic acid encoding the immunogenic polypeptides and fusion proteins in an expression vector are also disclosed.

The invention provides methods of inducing a transmission blocking antibody in a mammal. In the methods, the Pvs25-Pvs28 fusion protein, or a nucleic acid encoding the fusion protein is administered to a mammal, which produces transmission blocking antigens. Administration is typically performed intramuscularly, intradermally, or subcutaneously. An adjuvant such as alum is optionally administered with the fusion protein or nucleic acid.

A further understanding of the nature and advantages of the present invention may be realized by reference to the remaining portions of the specification, the figures and claims.

All publications, patents and patent applications cited herein are hereby expressly incorporated herein by reference for all purposes.

BRIEF DESCRIPTION OF THE DRAWINGS

FIG. 1 shows an exemplary polynucleotide sequence for a Pvs28 of the invention (SEQ ID NO:1).

FIG. 2 shows an exemplary Pvs28 polypeptide of the invention (SEQ ID NO:2).

FIG. 3 shows an exemplary polynucleotide sequence for a Pvs25 of the invention (SEQ ID NO:3).

FIG. 4 shows an exemplary Pvs25 polypeptide of the invention (SEQ ID NO:4).

FIG. 5 shows an exemplary Pvs28-Pvs25 fusion protein polypeptide of the invention (SEQ ID NO:5). GGGPGGG linker sequence=SEQ ID NO:15.

FIG. 6 shows exemplary constructs and recombinant proteins encoded by these constructs (Pvs25=SEQ ID NO:16; Pvs28=SEQ ID NO:17; Pvs28Q130=SEQ ID NO:18; Pvs28NCR=SEQ ID NO:19), including Pvs25, Pvs28, and partially deglycosylated Pvs28 (having a glutamine residue, rather than asparagine, at amino acid residue number 130).

FIG. 7 is a schematic representation of the an exemplary protocol for immunization of mice with recombinant forms of Pvs25 and Pvs28.

DEFINITIONS

To facilitate understanding the invention, a number of terms are defined below.

An "immunogen" refers to a compound or composition comprising a peptide, polypeptide or protein which is "immunogenic," i.e., capable of eliciting, augmenting or boosting a cellular and/or humoral immune response, either alone or in combination or linked or fused to another substance. An immunogenic composition can be a peptide of at least about 5 amino acids, a peptide of 10 amino acids in length, a fragment 15 amino acids in length, a fragment 20 amino acids in length or greater. The immunogen can comprise a "carrier" polypeptide and a hapten, e.g., a fusion protein or a carrier polypeptide fused or linked (chemically or otherwise) to another composition (described below). The immunogen can be recombinantly expressed in an immunization vector, which can be simply naked DNA comprising the immunogen's coding sequence operably linked to a promoter, e.g., a simple expression cassette. The immunogen includes antigenic determinants, or epitopes (described below), to which antibodies or TCRs bind, which are typically 3 to 10 amino acids in length.

The term "Pvs25" and "Pvs28" polynucleotide refers to nucleic acid molecules which encode Pvs25 and Pvs28 polypeptides, respectively, and nucleotides with substantial identity to these sequences, as described below. Pvs25 and Pvs28 polypeptides are polypeptides containing a sequence identical to or substantially identical (defined below) to the amino acid sequence of a class of 28 kD proteins expressed on the surface *Plasmodium vivax* ookinetes. An exemplary polynucleotide sequence for a Pvs28 of the invention is shown in SEQ ID NO:1, FIG. 1. An exemplary amino acid sequence for a Pvs28 polypeptide of the invention is shown in SEQ ID NO:2, FIG. 2. An exemplary polynucleotide sequence for a Pvs25 of the invention is shown in SEQ ID NO:3, FIG. 3. An exemplary amino acid sequence for a Pvs25 polypeptide of the invention is shown in SEQ ID NO:4, FIG. 4. The term "Pvs25" and "Pvs28 polypeptide" encompasses native proteins as well as recombinantly produced modified proteins that induce an immune response, including a transmission blocking immune response. It also includes immunologically active fragments of these proteins. The terms "Pvs25" and "Pvs28 polypeptide" also encompasses partially or completely deglycosylated forms. A Pvs25 and Pvs28 polypeptide of the invention can be full length or an immunologically active fragment. The polypeptides will typically be between about 30 and 200 amino acids, typically at least about 100 amino acids in length. Typically Pvs25 and Pvs28 polypeptides are characterized by their ability to induce transmission blocking immune responses, alone, or, as Pvs25/Pvs28 fusion proteins. The term "Pvs25" and "Pvs28 polypeptide" encompasses homologues and allelic variants of Pvs28 or Pvs25. Such homologues, also referred to as Pvs28 or Pvs25 polypeptides, respectively, include variants of the native proteins constructed by in vitro techniques, and proteins from parasites related to *P. vivax* and *P. falciparum*. For example, one skilled in the art will appreciate that for certain uses it is advantageous to produce a Pvs28 or Pvs25 polypeptide sequence that is lacking a structural characteristic; e.g., one may remove a transmembrane domain to obtain a polypeptide that is more soluble in aqueous solution. The Pvs25 and Pvs28 polypeptides of the invention, and sequences encoding these proteins, also include fusion proteins comprising nonmalarial sequences, e.g., epitope tags, enzyme cleavage recognition sequences, signal sequences, secretion signals (e.g., yeast alpha mating pheromone signal sequence) and the like.

In the expression of recombinant genes, such as expression cassette or vector-expressed sequences or transgenes, one of skill will recognize that the inserted polynucleotide sequence need not be identical and may be "substantially identical" to a sequence of the gene from which it was derived. As explained below, these variants are specifically covered by the term Pvs25 and Pvs28. These variations include partially or completely deglycosylated forms of the polypeptides, and the nucleic acids which encode these variations.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the above term. In addition, the term "polynucleotide sequence from a Pvs25 (or Pvs28) gene" specifically includes those sequences substantially identical (determined as described below) with a Pvs25 or Pvs28 gene sequence and that encode proteins that retain the function of the Pvs25 or Pvs28 protein, respectively. Thus, in the case of the Pvs25 and Pvs28 gene disclosed herein, the above term includes variant polynucleotide sequences which have substantial identity with the sequences disclosed here and which encode proteins capable of inducing an immune response, such as, but not limited to, a transmission blocking immune response.

A "fusion protein" refers to a composition comprising at least one polypeptide or peptide domain which is associated with a second domain. The second domain can be a polypeptide, peptide, polysaccharide, or the like. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common message. Alternatively, the compositions of the domains can be linked by any chemical or electrostatic means. The Pvs25 and Pvs28 fusion proteins of the invention can also include non-malarial sequences, e.g., linkers, epitope tags, enzyme cleavage recognition sequences, signal sequences, secretion signals, and the like.

A "Pvs25-Pvs28 fusion protein" refers to a polypeptide comprising at least two domains, with polypeptide subsequences derived from both Pvs25 and Pvs28. The fusion protein, in alternative embodiments, typically includes about 10 contiguous amino acids or more; 15 contiguous amino acids or more; 20 contiguous amino acids or more; and 25 contiguous amino acids or more from both Pvs25 and Pvs28. The Pvs25-Pvs28 fusion protein can comprise additional subsequences which are not derived from Pvs25 or Pvs28, such as a flexible linker region separating the Pvs25 and Pvs28 subsequences, epitope tags, etc., as discussed above.

An "N terminal" or "C terminal" domain in reference to a specified protein refers to a polypeptide subsequence derived from the N terminal or C terminal half of the indicated protein. For example, an N terminal Pvs25 protein domain refers to a polypeptide subsequence derived from the N terminal half of the Pvs25 protein. Similarly, a C terminal Pvs28 protein domain refers to a polypeptide subsequence derived from the C terminal half of the Pvs28 protein. The subsequence is from about 10 amino acids in length up to the entire specified half protein.

The term "subsequence" in the context of a particular nucleic acid sequence or polypeptide refers to a region of the nucleic acid or polypeptide equal to or smaller than the specified nucleic acid or polypeptide.

A "recombinant nucleic acid" comprises or is encoded by one or more nucleic acids that are derived from a nucleic acid which was artificially constructed. For example, the nucleic acid can comprise or be encoded by a cloned nucleic acid formed by joining heterologous nucleic acids as taught, e.g., in Berger and Kimmel, Guide to Molecular Cloning Techniques, Methods in Enzymology volume 152 Academic Press, Inc., San Diego, Calif. (Berger) and in Sambrook et al. (1989) Molecular Cloning—A Laboratory Manual (2nd ed.) Vol. 1-3 (Sambrook). Alternatively, the nucleic acid can be synthesized chemically. The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell or a progenitor of the cell by artificial means.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

The nucleic acid and polypeptide sequences of the invention includes gene and protein products, respectively, identified and characterized by analysis of Pvs 25 and Pvs28 sequences of the nucleic acids and proteins of the invention. Optimal alignment of sequences for comparison can use any means to analyze sequence identity (homology) known in the art, e.g., by the progressive alignment method of termed "PILEUP" (see below); by the local homology algorithm of Smith & Waterman, Adv. Appl. Math. 2: 482 (1981); by the homology alignment algorithm of Needleman & Wunsch, J. Mol. Biol. 48:443 (1970); by the search for similarity method of Pearson (1988) Proc. Natl. Acad. Sci. USA 85: 2444; by computerized implementations of these algorithms (GAP, BESTFIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by Higgins (1988) Gene, 73: 237-244; Corpet (1988) Nucleic Acids Res. 16:10881-90; Huang (1992) Computer Applications in the Biosciences 8:155-65, and Pearson (1994) Methods in Molec. Biol. 24:307-31), TreeAlign, MALIGN, and SAM sequence alignment computer programs; or, by inspection. See also Morrison (1997) Mol. Biol. Evol. 14:428-441, as an example of the use of PILEUP. PILEUP, creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987). The method used is similar to the method described by Higgins & Sharp (1989) CABIOS 5: 151-153. The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

Another example of algorithm that is suitable for determining sequence similarity is the BLAST algorithm, which is described in Altschul (1990) J. Mol. Biol. 215: 403-410. Software for performing BLAST analyses is publicly available through the National Center for Biotechnology Information, available on the worldwide web at ncbi.nlm.nih.gov/; see also Zhang (1997) Genome Res. 7:649-656 (1997) for the "PowerBLAST" variation. This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11,the BLOSUM62 scoring matrix (see Henikoff (1989) Proc. Natl. Acad. Sci. USA 89:10915) alignments (B) of 50, expectation (E) of 10, M=5, N=-4, and a comparison of both strands. The BLAST algorithm performs a statistical analysis of the similarity between two sequences (see, e.g., Karlin (1993) Proc. Natl. Acad. Sci. USA 90: 5873-5787). One measure of similarity provided by the BLAST algorithm is the smallest sum probability (P(N)), which provides an indication of the probability by which a match between two nucleotide or amino acid sequences would occur by chance.

"Percentage of sequence identity" is determined by comparing two optimally aligned sequences over a comparison window, wherein the portion of the polynucleotide sequence in the comparison window may comprise additions or deletions (i. e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 80% sequence identity, preferably at least 85%, more preferably at least 90% and most preferably at least 95%, compared to a reference sequence, the programs described above using standard parameters. Thus, if a sequence has about 80% sequence homology to a known Psv25 or Pvs28 polynucleotide or variant thereof, then that sequence is considered a specie of Pvs25 or Pvs28, respectfully. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for these purposes means sequence identity of at least 40%, preferably at least 60%, more preferably at least 90%, and most preferably at least 95%. Thus, if a sequence has about 40% sequence homology to a known Psv25 or Pvs28 polypeptide or variant thereof, then that sequence is considered a specie of Psv25 or Pvs28, respectfully. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, asp artic acid-glutamic acid, and asparagine-glutamine.

Determination of "substantial identity" can be focused over defined subsequences, such as known structural domains. For example, for Pfs25 and Pvs28, another measure of structural similarity will be the striking alignment of cysteine (cys) residues and the spacing between the cys residues.

The reason why these residues are of higher importance than others is that they are critically involved in recreating the disulfide bond arrangements that comprise the EGF-like domains. These domains are the hallmarks of Pvs25 and Pvs28, as with the related *Plasmodium* polypeptides Pfs25 and Pfs28.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 1 molar at pH 7 and the temperature is at least about 60° C.

In the present invention, mRNA encoded by the nucleic acids of the invention can be identified in Northern blots under stringent conditions using the sequences disclosed here or fragments of, typically, at least about 100 nucleotides. For the purposes of this disclosure, stringent conditions for such RNA-DNA hybridizations are those which include at least one wash in 6×SSC for 20 minutes at a temperature of at least about 50° C., usually about 55° C. to about 60° C., or equivalent conditions.

Another indication that protein sequences are substantially identical is if one protein is immunologically reactive with antibodies raised against the other protein. Thus, the proteins of the invention include proteins immunologically reactive with antibodies raised against Pvs 25 and Pvs28 polypeptides, and fusion proteins thereof.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine, and UGG, the single codon for Trp) can be modified to yield a functionally identical molecule by standard techniques. Accordingly, each "silent variation" of a nucleic acid which encodes a polypeptide is implicit in each described sequence.

The term "conservatively modified variations" refers to individual substitutions, deletions or additions which alter, add or delete a single amino acid or a small percentage of amino acids (typically less than 5%, more typically less than 1%) in an encoded sequence, where the alterations result in the substitution of an amino acid with a chemically similar amino acid; and the alterations, deletions or additions do not alter the structure, function and/or immunogenicity of the sequence. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A "vector" is a composition which can transduce, transfect, transform or infect a cell, thereby causing the cell to replicate or express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell, nor that any particular cell type is the subject of transduction. A cell is "transformed" by a nucleic acid when the nucleic acid is transduced into the cell and stably replicated. A vector includes a nucleic acid (ordinarily RNA or DNA) to be expressed by the cell. This nucleic acid is optionally referred to as a "vector nucleic acid." A vector optionally includes materials to aid in achieving entry of the nucleic acid into the cell, such as a viral particle, liposome, protein coating or the like. A "cell transduction vector" is a vector which encodes a nucleic acid which is expressed in a cell once the nucleic acid is transduced into the cell.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "susceptible organism" is a *Plasmodium* host that is susceptible to malaria, for example, humans and chickens. The particular susceptible organism or host will depend upon the *Plasmodium* species.

As used herein, "isolated," when referring to a molecule or composition, such as, e.g., a Pvs25 or Pvs28 nucleic acid or polypeptide, means that the molecule or composition is separated from at least one other compound, such as a protein, other nucleic acids (e.g., RNAs), or other contaminants with which it is associated in vivo or in its naturally occurring state. Thus, a Pvs25 or Pvs28 composition is considered isolated when the Pvs25 or Pvs28 has been isolated from any other component with which it is naturally associated, e.g., cell membrane, as in a cell extract. An isolated composition can, however, also be substantially pure. An isolated composition can be in a homogeneous state and can be in a dry or an aqueous solution. Purity and homogeneity can be determined, for example, using analytical chemistry techniques such as polyacrylamide gel electrophoresis (SDS-PAGE) or high performance liquid chromatography (HPLC). Thus, the isolated Pvs25 or Pvs28 compositions of this invention do not contain materials normally associated with their in situ environment. Even where a protein has been isolated to a homogenous or dominant band, there are trace contaminants which co-purify with the desired protein.

A "transmission blocking antibody" is an antibody which inhibits the growth or replication of a malarial parasite during the sexual stage of parasite development in the mosquito gut. The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplar immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. Antibodies exist e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, Fundamental Immunology, Third Edition, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies. Immunoglobulins generated using recombinant expression libraries are also antibodies for purposes of this invention.

An "immunogenic composition" is a composition which elicits the production of antibodies or a cell-mediated immune response when administered to a mammal.

An "immunological carrier" or "carrier" in the immunological context (as opposed to a carrier which is a nonactive composition for the purpose of formulating, storing or carrying a pharmaceutical) is an composition which, when linked, joined, chemically coupled or fused to a second composition (e.g., protein, peptide, polysaccharide or the like) boosts or augments the cellular or humoral response to the composition. Any physiologic mechanism can be involved in this augmentation or boosting of the immune response. An immunogenic carrier is typically a polypeptide linked or fused to a second composition of interest comprising a protein, peptide or polysaccharide, where the carrier stimulates a cellular (T cell mediated) immune response that boosts or augments the humoral (B cell mediated, antibody-generating) immune response to the composition of interest. These second compositions can be "haptens," which are typically defined as compounds of low molecular weight that are not immunogenic by themselves, but that, when coupled to carrier molecules, can elicit antibodies directed to epitopes on the hapten. For example, the lack of an adequate immune response to the major polysaccharide of the *Haemophilus influenzae* type b capsule (PRP) in very young infants can be overcome by conjugating PRP to a T-cell dependent carrier protein (see Zepp (1997) Eur. J. Pediatr. 156:18-24). Alternatively, a peptide can be linked to a carrier simply to facilitate manipulation of the peptide in the generation of the immune response (see, e.g., Rondard (1997) Biochemistry 36:8962-8968).

An "epitope" refers to an antigenic determinant or antigen site that interacts with an antibody or a T cell receptor (TCR). An "antigen" is a molecule or composition that induces the production of an immune response. An antibody or TCR binds to a specific conformational (possibly charge-dependent) domain of the antigen, called the "antigenic determinant" or "epitope" (TCRs bind the epitope in association with a third molecule, a major histocompatibility complex (MHC) protein).

DETAILED DESCRIPTION

The present invention relates to novel compositions and methods for blocking transmission of malaria, particularly *Plasmodium vivax*. The invention provides agents which are capable eliciting antibodies and antiserum (generated by administration of the compositions of the invention) which, when ingested by the mosquito, are capable of inhibiting the life cycle of the disease-causing parasite in the mosquito midgut. The agents include *Plasmodium vivax* Pvs 25 and Pvs28 polypeptides (including partially and completely deglycosylated forms), nucleic acids encoding these polypeptides, and fusion proteins thereof, that are useful for inducing antibodies that block transmission of the parasite. The invention also provides the isolated antibodies generated by these polypeptides. These nucleic acid and polypeptide compositions are useful as vaccines against malaria.

This invention further relates to an immunogenic composition capable of eliciting an immunogenic response directed to an epitope comprising an isolated Pvs25 or Pvs28 and an isolated molecule comprising the epitope. The invention is also directed to methods of eliciting an immunogenic response directed to an epitope comprising administering an isolated Pvs28 and an isolated molecule comprising the epitope. In one embodiment, the Pvs28 is acting as an immunogenic carrier to a hapten epitope to elicit, stimulate or augment a humoral immune response to the epitope.

The fusion proteins of the invention (optionally used with an adjuvant such as alum) can be used to block transmission of a number of parasites associated with malaria. Examples of parasites whose transmission is blocked by the materials and compositions of the invention include the causative parasites for malaria. Four species of the genus *Plasmodium* infect humans, *P. vivax, P. ovale, P. malariae*, and *P. falciparum*. *P. falciparum* is the most prevalent cause of malaria in humans: Other *Plasmodium* species infect other animals. For instance, *P. gallinaceum* is responsible for avian malaria.

The present invention relates to recombinant viruses and vaccines comprising nucleic acid sequences which encode malaria parasite (*Plasmodium vivax*) Pvs25 and Pvs28 polypeptides, including fusion proteins and deglycosylated forms (SEQ ID NOs: 1 to 5). These polypeptides are naturally expressed by *Plasmodium* during its mosquito-infective, sexual stage. Because naturally expressed Pvs polypeptides are expressed in malaria parasite oocytes and zygotes, recombinant forms can be used to induce an immune response to the sexual stage of the parasite.

These Pvs25- and Pvs28-expressing malaria parasite sexual stages occur only in the mosquito host and not in the human. This invention includes compositions and methods for eliciting human antibodies which, when ingested by the mosquito during its feeding process, block the development of malaria in the mosquito. Blocking the sexual development of the malaria parasite in the mosquito reduces the vector's ability to further transmit the disease to a second human host.

The human antiserum generated by the compositions and methods of the invention, when ingested by the mosquito, significantly reduces the numbers of malaria parasite oocysts within the insect. Significant public health benefits are attained by the vaccines' ability to elicit antibodies which, upon mosquito ingestion, significantly decrease the number of oocysts capable of maturing into infectious sporozoites. A vaccine is still very useful when it generates an antiserum that decreases the numbers of oocysts in the mosquito, thus reducing the numbers of parasites transmitted by the mosquito. To be useful, it is not necessary that the ingested antisera render the mosquito completely incapable of transmitting the malaria parasite to a second person (i.e., completely inhibit sexual development of all oocysts).

The use of sexual stage polypeptides as a transmission blocking antigens are described, e.g., in U.S. Pat. No. 5,217,898 to Kaslow and Barr directed to Pfs25 as a transmission blocking antigen, and U.S. Pat. No. 5,527,700 to Kaslow and Duffy, directed to Pfs28 as a transmission blocking antigen.

The Pvs25-Pvs28 fusion proteins of the invention have several surprising properties. The fusion protein is more efficient in producing transmission blocking antibodies, e.g., in mice, than Pvs25 or Pvs28 alone. This is true despite the fact a mixed dose of Pvs25 and Pvs28 will not induce a higher level of transmission blocking antibody activity than either Pvs25 or Pvs28 alone. Second, less fusion protein is required as an immunogen than either Pvs25 or Pvs28 alone. Third, titers of transmission blocking antibodies will remain high for a longer period of time when the antigen is a Pvs25-Pvs28 fusion protein than either Pvs25 or Pvs28 alone. In a preferred aspect, the invention provides a nucleic acid with yeast preferred codons for encoding and expressing the fusion protein in yeast.

Pvs28 and Pvs25 Polypeptides

The present invention includes immunogenic Pvs 25 and Pvs28 polypeptides and fragments derived from these proteins, and partially or completely deglycosylated forms of these polypeptides, that are useful for inducing an immune response when the proteins are injected into a human or other host animal. An exemplary polynucleotide sequence for a Pvs25 of the invention is shown in SEQ ID NO:3, FIG. 3. An exemplary amino acid sequence for a Pvs25 polypeptide of the invention is shown in SEQ ID NO:4, FIG. 4. An exemplary polynucleotide sequence for a Pvs28 of the invention is shown in SEQ ID NO:1, FIG. 1. An exemplary amino acid sequence for a Pvs28 polypeptide of the invention is shown in SEQ ID NO:2, FIG. 2.

In another embodiment, the immunogenic composition, comprising an isolated Pvs28 and an isolated molecule comprising the epitope, is capable of eliciting or augmenting an immunogenic response directed to the epitope. The Pvs28 can act as a immunological "carrier" to boost, augment or increase the cellular or humoral response to the epitope. The antibodies that arise from the immune response block transmission of the parasite by interfering with the portion of the parasite's life cycle that occurs in the mosquito. For example, purified polypeptides having an amino acid sequence substantially identical to a subsequence of Pvs28 may be used; including partially or completely deglycosylated forms of Pvs28.

The antibodies or T cells that arise from administration of Pvs28, Pvs25 or Pvs28-Pvs25 fusion proteins (e.g., as in a polypeptide vaccine, or a vaccine comprising nucleic acid encoding these polypeptides, such as a virus or vector) generate an immune response by blocking transmission of the parasite malaria by interfering with the portion of the parasite's life cycle that occurs in the mosquito. Pvs 25 and Pvs28 are similar in structure to other known ookinete antigens such as Pfs25 and Pfs28, respectively. All four proteins comprise a putative secretory signal sequence, followed by four EGF-like domains and a terminal hydrophobic transmembrane region without a cytoplasmic tail. Although the four proteins share the six-cysteine motif of the EGF-like domains, the functions of these proteins may be very different. EGF-like domains have been recognized in a range of proteins that have diverse functions (Davis (1990) New Biol. 2:410-419).

Included among the polypeptides of the present invention are proteins that are variants of the native proteins constructed by in vitro or in vivo techniques, including recombinant or synthetic techniques. One skilled in the art will appreciate, for instance, that for certain uses it would be advantageous to produce a Pvs25 or a Pvs28 polypeptide that is lacking one of its structural characteristics. For example, one may remove the transmembrane domain to obtain a polypeptide that is more soluble in aqueous solution.

Alternatively, the invention provides partially and completely deglycosylated variants, such as the genetically engineered Pvs28 of the invention in which the amino acid at position 130 does not encode an asparagine, and thus cannot be a putative site for N-linked glycosylation. In an exemplary sequence, the nucleic acid of the invention was modified to encode glutamine, and the Pvs28 variant polypeptide of the invention was modified to be glutamine at residue 130. However, any putative amino acid site of N— or O-linked glycosylation (and the nucleic acid which encodes such a site, or motif) can be modified to alternatively be (or encode, in the case of the nucleic acid) any amino acid residue incapable of acting as a glycosylation signal.

The Pvs28 and Pvs25 proteins of the invention may be purified from parasites isolated from infected host organisms. For a review of standard techniques see, e.g., Methods in Enzymology, "Guide to Protein Purification", M. Deutscher, ed. Vol. 182 (1990); Scopes, R. K., Protein Purification: Principles and Practice, 2nd ed., Springer Verlag, (1987). For instance, Pvs25 and Pvs28 polypeptides can be purified using affinity chromatography, SDS-PAGE, and the like. Illustrative examples of methods for purifying Pvs25, Pvs28 and fusion proteins thereof of the invention are described below. Methods for purifying desired proteins are well known in the art and are not presented in detail here.

Solubility Fractionation

If the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic of proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

If the size of the protein of interest is known or can be estimated from the cDNA sequence, proteins of greater and lesser size can be removed by ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed.

Column Chromatography

Proteins can be separated on the basis of their size, net surface charge, hydrophobicity and affinity for ligands. In addition, antibodies raised against proteins can be conjugated to column matrices and the proteins immunopurified. All of these general methods are well known in the art. See Scopes (1987) supra. Chromatographic techniques can be performed at any scale and using equipment from many different manufacturers (e.g., Pharmacia Biotech). Protein concentrations can be determined using any technique, e.g., as in Bradford (1976) Anal. Biochem. 72:248-257.

Amino Acid Sequence Determination

Illustrative amino acid sequences of the Pvs28 and Pvs25 and fusion proteins of this invention can be determined by, for example, Edman degradation, a technique which is well known in the art. In addition to the internal sequencing (see also Hwang (1996) J. Chromatogr. B. Biomed. Appl. 686: 165-175), N-terminal sequencing can be performed by techniques known in the art. For C-terminal sequence determination, a chemical procedure for the degradation of peptides and analysis by matrix-assisted-laser-desorption ionization mass spectrometry (MALDI-MS) can be used Thiede (1997) Eur. J. Biochem. 244:750-754.

Molecular Weight/Isoelectric Point Determination

The molecular weight of a protein can be determined by many different methods, all known to one of skill in the art. Some methods of determination include: SDS gel electrophoresis, native gel electrophoresis, molecular exclusion chromatography, zonal centrifugation, mass spectroscopy, and calculation from sequencing. Disparity between results of different techniques can be due to factors inherent in the technique. For example, native gel electrophoresis, molecular exclusion chromatography and zonal centrifugation depend on the size of the protein. The proteins that are cysteine rich can form many disulfide bonds, both intra- and intermolecular. SDS gel electrophoresis depends on the binding of SDS to amino acids present in the protein. Some amino acids bind SDS more tightly than others, therefore, proteins will migrate differently depending on their amino acid composition. Mass spectroscopy and calculated molecular weight from the sequence in part depend upon the frequency that particular amino acids are present in the protein and the molecular weight of the particular amino acid. If a protein is glycosylated, mass spectroscopy results will reflect the glycosylation but a calculated molecular weight may not.

The isoelectric point of a protein can be determined by native gel (or disc) electrophoresis, isoelectric focussing or in a preferred method, by calculation given the amino acid content of the protein (see, for example, Wehr (1996) Methods Enzymol. 270:358-374; Moorhouse (1995) J. Chromatogr. A. 717:61-69, describing capillary isoelectric focusing).

Pvs25-Pvs28 Fusion Proteins

The present invention includes immunogenic polypeptides which comprise polypeptide subsequences derived from both Pvs28 and Pvs25, including the exemplary fusion protein of the invention SEQ ID NO:5 (see FIG. 5) and deglycosylated forms. These polypeptides are useful for inducing an immune response when the fusion protein is injected into a human, mouse or other host animal. The antibodies that arise from the immune response block transmission of the malarial parasite by interfering with the portion of the parasite's life cycle that occurs in the mosquito.

The fusion proteins typically include an immunogenic domain, or epitope, from a Pvs25 and an immunogenic domain, or epitope from a Pvs28 (including deglycosylated forms). The immunogenic domains, or epitopes, are peptide and polypeptide subsequences of the corresponding polypeptides which are sufficient to elicit an immunogenic response (antibody or T cell response) against the domain when administered to a mammal (e.g., a mouse or a human). In one embodiment, the immunogenic domain can elicit the production of an antibody which recognizes the corresponding full length protein. For example, if the immunogenic domain is a Pvs25 subsequence, the domain (epitope) elicits the production of an antibody which specifically binds to Pvs25. Similarly, if the immunogenic domain is a Pvs28 subsequence, the domain preferably elicits the production of an antibody which specifically binds to Pvs28.

To elicit the production of an antibody, the immunogenic domain is typically at least about 3-10 amino acids in length, because the protein recognition site on an antibody typically recognizes an amino acid of about 3-10 amino acids in length. More often, the immunogenic domain is longer than 10 amino acids, and the domain optionally includes the full length sequence of the corresponding protein (i.e., in one embodiment, the Pvs25-Pvs28 fusion protein comprises the complete sequence of both Pvs25 and Pvs28). Ordinarily, only a fraction of the full length protein is included. In one embodiment, about 10% of the full length Pvs25 is included in the fusion protein. In another embodiment, about 20% of the full length Pvs25 is included in the fusion protein. In yet another embodiment, about 30% of the full length protein is included. In still another embodiment, about 40% of the full length Pvs25 is included in the fusion protein. Optionally, as much as about 50% of the full length Pvs25 is included in the fusion protein. Occasionally, as much as about 60% of the full length Pvs25 is included in the fusion protein. In some embodiments, as much as about 70% of the full length Pvs25 is included in the fusion protein. In one class of embodiments, as much as about 80% of the full length Pvs25 is included in the fusion protein. As much as about 90% of the full length Pvs25 is optionally included in the fusion protein. As already mentioned, the entire full length Pvs25 protein is optionally incorporated into the fusion protein.

Similarly, in one embodiment, about 10% of the full length Pvs28 is included in the fusion protein. In another embodiment, about 20% of the full length Pvs28 is included in the fusion protein. In yet another embodiment, about 30% of the full length protein is included. In still another embodiment, about 40% of the full length Pvs28 is included in the fusion protein. Optionally, as much as about 50% of the full length Pvs28 is included in the fusion protein. Occasionally, as much as about 60% of the full length Pvs28 is included in the fusion protein. In some embodiments, as much as about 70% of the full length Pvs28 is included in the fusion protein. In one class of embodiments, as much as about 80% of the full length Pvs28 is included in the fusion protein. As much as about 90% of the full length Pvs28 is optionally included in the fusion protein. As already mentioned, the entire full length Pvs28 protein is optionally incorporated into the fusion protein.

The portion of the Pvs25 or Pvs28 protein from which the immunogenic domain, or epitope, is selected is optionally optimized for maximum immunogenicity for the induction of transmission blocking vaccines. Any combination of Pvs25 and Pvs28 subsequences (epitopes) can be combined. Any combination of complete or partially deglycosylated subsequences can be combined. In alternative embodiments, the Pvs25 and Pvs28 epitopes can be in alternating or sequential patterns. For example, in one embodiment, the carboxyl terminal portion of Pvs28 is included. Embodiments also include those derived from fusion proteins in which about 10-20 amino acids are deleted or added to the particular Pvs25 or Pvs28 subsequences described. The added or deleted amino acids are added or deleted by reference to the corresponding full length sequence, e.g., where the subsequence is derived from Pvs25, a 10-20 amino acid sequence derived from Pvs25 is optionally added to either end of the subsequence.

The fusion proteins optionally includes additional features such as a flexible linker between Pvs25 and Pvs28 domains. The linkers can facilitate the independent folding of the Pvs25 and Pvs28 proteins. Preferred flexible linkers are amino acid subsequences which are synthesized as part of a recombinant fusion protein. In one embodiment, the flexible linker is an amino acid subsequence comprising a proline such as $Gly_3$-Pro-$Gly_3$ (SEQ ID NO:15). In other embodiments, a chemical linker is used to connect synthetically or recombinantly produced Pvs25 and Pvs28 subsequences. Such flexible linkers are known to persons of skill in the art. For example, poly (ethylene glycol) linkers are available from Shearwater Polymers, Inc. Huntsville, Ala. These linkers optionally have amide linkages, sulfhydryl linkages, or heterofunctional linkages.

In addition to flexible linkers, the fusion proteins optionally include polypeptide subsequences from proteins which are unrelated to Pvs25 or Pvs28, e.g., a sequence with affinity to a known antibody to facilitate affinity purification, detection, or the like. Such detection- and purification-facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and Pvs25 or Pvs28 protein(s) may be useful to facilitate purification. One such expression vector provides for expression of a fusion protein comprising the sequence encoding a Pvs25 or Pvs28 of the invention, or a fusion protein thereof, and nucleic acid sequence encoding six histidine residues followed by thioredoxin and an enterokinase cleavage site (for example, see Williams (1995) Biochemistry 34:1787-1797). The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the patent and scientific literature, see e.g., Kroll (1993) DNA Cell. Biol., 12:441-53).

An exemplary fusion of Pvs25 to Pvs28 by a flexible linker is represented by the polypeptide of FIG. 5, SEQ ID NO:5, whose individual domains are:

a Pvs25 sequence (with or without a signal sequence or anchor):

```
AVTVDTICKNGQLVQMSNHFKCMCNEGLVHLSENTC    (SEQ ID NO:20)
EEKNECKKETLGKACGEFGQCIENPDDPAQVNMYKCG
CIEGYTLKEDTCVLDVCQYKNCGESGECIVEYLSEI
QSAGCSCAIGKVPNPEDEKKCTKTGETACQLKCNTD
NEVCKNVEGVYKCQCMEGFTFDKEKNVCLS;
``` with a flexible linker, e.g.: GGGPGGG (SEQ ID NO:15); and a Pvs28 sequence (with or without signal sequence or anchor):

```
AKVTAETQCKNGYVVQMSNHFECKCNDGFVMANENT    (SEQ ID NO:21)
CEEKRDCTNPQNVNKNCGDYAVCANTRMNDEERALR
CGCILGYTVMNEVCTPNKCNGVLCGKGKCILDPANV
NSTMCSCNIGTTLDESKKCGKPGKTECTLKCKANEE
CKETQNYYKCVAKGSGGEGSGGEGSGGEGSGGEGSG
GEGSGGDTGAAYSLMN.
```

The fusion protein (and a Pvs25 or Pvs28 polypeptide) can also include a secretory signal sequence, e.g., in mammalian cell expression: Ig secretion signal or tPA signal sequence; or a pre-pro secretion signal, e.g., in yeast: alpha-factor.

Included among the polypeptides of the present invention are fusion proteins that have subsequences which are homologues or allelic variants of Pvs28 or Pvs25. Such homologues, also referred to as Pvs28 or Pvs25 polypeptides, respectively, include variants of the native proteins constructed by in vitro techniques, and proteins from parasites related to P. vivax and P. falciparum. For example, one skilled in the art will appreciate that for certain uses it is advantageous to produce a Pvs28 or Pvs25 polypeptide subsequence that is lacking a structural characteristic; e.g., one may remove a transmembrane domain (to obtain a polypeptide that is more soluble in aqueous solution) or a glycosylation site (to obtain a polpeptide that is more antigenic under certain conditions).

One of skill will appreciate that many conservative variations of the fusion proteins and nucleic acid which encode the fusion proteins yield essentially identical products. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. As described herein, sequences are preferably optimized for expression in a particular host cell used to produce the fusion protein (e.g., yeast). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention.

One of skill will recognize many ways of generating alterations in a given nucleic acid sequence, which optionally provides alterations to an encoded protein. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) Gene 8:81-97; Roberts et al. (1987) Nature 328:731-734 and Sambrook, Innis, Ausbel, Berger, Needham VanDevanter and Mullis (below).

Most commonly, amino acid sequences are altered by altering the corresponding nucleic acid sequence and expressing the polypeptide. However, polypeptide sequences are also optionally generated synthetically on commercially available peptide synthesizers to produce any desired polypeptide (see, Merrifield, and Stewart and Young, supra).

One can select a desired nucleic acid or polypeptide of the invention based upon the sequences and constructs provided and upon knowledge in the art regarding malaria generally. The life-cycle, genomic organization, developmental regulation and associated molecular biology of malaria strains have been the focus of research since the advent of molecular biology.

Moreover, general knowledge regarding the nature of proteins and nucleic acids allows one of skill to select appropriate sequences with activity similar or equivalent to the nucleic acids, vectors and polypeptides disclosed herein. The definitions section herein describes exemplar conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

Pvs25 Pvs28 and Pvs25-Pvs28 Nucleic Acids

Another aspect of the present invention relates to the cloning and recombinant expression (using expression cassettes, plasmids, vectors, recombinant viruses, and the like) of Pvs 25 and Pv28 proteins, variants (i.e. deglycosylated forms) construction of Pvs25-Pvs28 fusion proteins, as described above. The recombinantly expressed proteins can be used in a number of ways. For instance, they can be used as transmission-blocking vaccines or as immunogens to raise antibodies, as described below. In addition, oligonucleotides from the cloned genes can be used as probes to identify homologous, allelic and variant species of Pvs polypeptides in Plasmodium vivax, Plasmodium sp., and in other species.

Thus, the invention relies on routine techniques in the field of recombinant genetics, well known to those of ordinary skill in the art and well described in the scientific and patent literature, e.g., basic texts disclosing the general methods of use in this invention include Berger and Kimmel, Guide to Molecular Cloning Techniques, Methods in Enzymology volume 152 Academic Press, Inc., San Diego, Calif. (Berger); Sambrook et al., Molecular Cloning, A Laboratory Manual, Cold Spring Harbor Publish., Cold Spring Harbor, NY 2nd ed. (1989) (Sambrook); and Current Protocols in Molecular Biology, F. M. Ausubel et al., eds., Current Protocols, Greene Publishing Associates, Inc. and John Wiley & Sons, Inc. (1995 Supplement). Product information from manufacturers of biological reagents and experimental equipment also provide information useful in known biological methods. Such manufacturers include, e.g., the SIGMA chemical company (Saint Louis, MO), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

In summary, the manipulations necessary to prepare nucleic acid segments encoding the polypeptides and introduce them into appropriate host cells involve 1) purifying the polypeptide from the appropriate sources, 2) preparing degenerate oligonucleotide probes corresponding to a portion of the amino acid sequence of the purified proteins, 3) screening a cDNA or genomic library for the sequences which hybridize to the probes, 4) constructing vectors comprising the sequences linked to a promoter and other sequences necessary for expression and 5) inserting the vectors into suitable host cells or viruses.

After isolation of the desired protein as described above, the amino acid sequence of the N-terminus is determined and degenerate oligonucleotide probes, designed to hybridize to the desired gene, are synthesized. Amino acid sequencing is performed and oligonucleotide probes are synthesized according to standard techniques as described, e.g., in Sambrook or Ausubel.

Genomic or cDNA libraries are prepared according to standard techniques as described, e.g., in Sambrook or Ausubel. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and plasmids.

To prepare cDNA, mRNA from the parasite of interest is first isolated. Eukaryotic mRNA has at its 3' end a string of adenine nucleotide residues known as the poly-A tail. Short chains of oligo d-T nucleotides are then hybridized with the poly-A tails and serve as a primer for the enzyme, reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or phage vector for propagation in *E. coli*.

cDNA can also be prepared using PCR (see below for further discussion PCR). PCR is used to produce high-quality cDNA from nanograms of total or poly A+ RNA. For example, the CapFinder™ PCR cDNA Synthesis Kit (Clonetech, Palo Alto, Calif.) was used to identify and isolate cDNA from *Plasmodium*. This technique utilizes long-distance PCR (Barnes (1994) Proc. Natl. Acad. Sci. USA 91:2216-2220, Cheng (1994) Proc. Natl. Acad. Sci. USA 91:5695-5699) to generate high yields of representative, double-stranded cDNA. See also, e.g., Zhu (July 1996) CLONTECHniques XI(3):12-13; CLONTECHniques (October 1995) X(4):2-5; and CLONTECHniques (January 1996) XI(1):2-4.

Identification of clones in either genomic or cDNA libraries harboring the desired nucleic acid segments is performed by either nucleic acid hybridization or immunological detection of the encoded protein, if an expression vector is used. The bacterial colonies are then replica plated on solid support, such as nitrocellulose filters. The cells are lysed and probed with either oligonucleotide probes described above or with antibodies to the desired protein.

Other methods well known to those skilled in the art are used to identify desired genes, i.e., various species of Pvs25 and Pvs28 of the invention. For example, the presence of restriction fragment length polymorphisms (RFLP) between wild type and mutant strains lacking a Pvs25 or Pvs28 polypeptide can be used.

Oligonucleotides can be used to identify and detect Pvs25 and Pvs28 using a variety of hybridization techniques and conditions. For example, amplification techniques, such as the polymerase chain reaction (PCR) can be used to amplify the desired nucleotide sequence. One of skill in the art will appreciate that, whatever amplification method is used, if a quantitative result is desired, care must be taken to use a method that maintains or controls for the relative frequencies of the amplified nucleic acids. Suitable amplification methods include, but are not limited to: polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., NY ("Innis"); and, U.S. Pat. Nos. 4,683,195 and 4,683,202 describe this method), ligase chain reaction (LCR) (Wu (1989) Genomics 4:560; Landegren (1988) Science 241:1077; Barringer (1990) Gene 89:117); transcription amplification (Kwoh Proc. Natl. Acad. Sci. USA, 86:1173 (1989)); and, self-sustained sequence replication (Guatelli (1990) Proc. Natl. Acad. Sci. USA, 87:1874); Q Beta replicase amplification (Smith (1997) J. Clin. Microbiol. 35:1477-1491, automated Q-beta replicase amplification assay; Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316, Sambrook, and Ausubel, as well as Mullis (1987) U.S. Pat. Nos. 4,683,195 and 4,683,202; Arnheim (1990) C&EN 36-47; Lomell J. Clin. Chem., 35:1826 (1989); Van Brunt, Biotechnology, 8:291-294 (1990); Wu (1989) Gene 4:560; Sooknanan (1995) Biotechnology 13:563-564. Methods for cloning in vitro amplified nucleic acids are described in Wallace, U.S. Pat. No. 5,426,039.

The invention provides for amplification and manipulation or detection of the products from each of the above methods to prepare DNA encoding a Pvs25 or Pvs28 protein specie. In PCR techniques, oligonucleotide primers complementary to the two borders of the DNA region to be amplified are synthesized an used (see, e.g., Innis). PCR can be used in a variety of protocols to amplify, identify, isolate and manipulate nucleic acids encoding Pvs25 or Pvs 28. In these protocols, appropriate primers and probes for identifying and amplifying DNA encoding Pvs25 or Pvs 28 polypeptides and fragments thereof are generated that comprise all or a portion of any of the DNA sequences listed herein. PCR-amplified sequences can also be labeled and used as detectable oligonucleotide probes, but such nucleic acid probes can be generated using any synthetic or other technique well known in the art, as described above. The labeled amplified DNA or other oligonucleotide or nucleic acid of the invention can be used as probes to further identify and isolate Pvs25 or Pvs 28 protein isoforms or alleles or Pvs25 or Pvs 28 from various cDNA or genomic libraries.

The present invention also provides RACE-based methods for isolating Pvs25 or Pvs 28 nucleic acids from any organism (RACE is another PCR-based approach for DNA amplification). Briefly, this technique involves using PCR to amplify a DNA sequence using a random 5' primer and a defined 3' primer (5' RACE) or a random 3' primer and a defined 5' primer (3' RACE). The amplified sequence is then subcloned into a vector where can be sequenced and manipulated using standard techniques. The RACE method is well known to those of skill in the art and kits to perform RACE are commercially available, e.g. Gibco BRL, Gaithersburg, Md., #18374-058 (5' RACE) or #18373-019 (3' RACE), see also Lankiewicz (1997) Nucleic Acids Res 25:2037-2038; Frohman (1988) Proc. Natl. Acad. Sci. USA 85:8998; Doenecke (1997) Leukemia 11:1787-1792.

For 5' RACE, a primer, the gene-specific primer, is selected near the 5' end of the known sequence oriented to extend towards the 5' end. The primer is used in a primer extension reaction using a reverse transcriptase and mRNA. After the RNA is optionally removed, the specifically-primed cDNA is either: 1) "tailed" with deoxynucleotide triphosphates (dNTP) and dideoxyterminal transferase, then a primer that is complimentary to the tail with a 5' end that provides a unique PCR site and the first gene-specific primer is used to PCR amplify the cDNA. Subsequent amplifications are usually performed with a gene-specific primer nested with respect to the first primer, or 2) an oligonucleotide that provides a unique PCR site is ligated to an end of the cDNA using RNA ligase; then a primer complimentary to the added site and the first gene-specific primer is used to PCR amplify the cDNA, with subsequent amplifications usually performed with a gene-specific primer nested with respect to the first primer. Amplified products are then purified, usually by gel electrophoresis then sequenced and examined to see contain the additional cDNA sequences desired.

For 3' RACE, an oligo dT-primer is annealed to the poly-A tails of an mRNA and then extended by a reverse transcriptase. Usually the oligo dT primer has a 5' end that provides a unique PCR site. The RNA is then removed, optionally, or dissociated, and the cDNA is amplified with a primer to the oligo dT tail and a gene-specific primer near the 3' end of the known sequence (oriented towards the 3' end). Subsequent amplifications are usually performed with a gene-specific primer nested with respect to the first primer. Amplified products are then purified, usually by gel electrophoresis then sequenced and examined to see contain the additional cDNA sequences desired.

Sequences amplified by PCR can be purified from agarose gels and cloned into an appropriate vector according to standard techniques.

Standard transfection methods are used to produce prokaryotic, mammalian, yeast or insect cell lines which express large quantities of the Pvs25 or Pvs 28 polypeptide, which is then purified using standard techniques, as described above. See, e.g., Colley (1989) J. Biol. Chem. 264:17619-17622; and Scopes, supra.

The polypeptides of the present invention can be readily designed and manufactured utilizing various recombinant DNA or synthetic techniques well known to those skilled in the art. For example, the polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including immunogenicity, facilitating purification, and preparation of the recombinant polypeptide. Design of completely or partially deglycosylated polypeptides improve the antigenicity of the immunogenic composition, as discussed above. Modified polypeptides can also be useful for modifying plasma half life, improving therapeutic efficacy, and lessening the severity or occurrence of side effects during therapeutic use. The amino acid sequence variants are usually predetermined variants not found in nature but exhibit the same, or improved (in the case of deglycosylation variants) immunogenic activity as naturally occurring, Pvs25 and Pvs28 polypeptides. For instance, polypeptide fragments comprising only a portion (usually at least about 60-80%, typically 90-95%) of the primary structure may be produced. For use as vaccines, polypeptide fragments are typically preferred so long as at least one epitope capable of eliciting transmission blocking antibodies remains. In the construction of deglycosylation variants, amino acid motifs which act as N-linked or O-linked glycosylation signals (which are well known in the art, see, e.g., Kakinuma (1997) J Biol Chem 272:28296-28300) are modified to forms (motif variants) that are not recognized as glycosylation sites in the expression systems in which the recombinant form is produced.

The nucleotide sequences used to express the polypeptides of the invention and to transfect the host cells can be modified according to standard techniques to yield Pvs25-Pvs28, Pvs25 or Pvs28 polypeptides, fusion proteins, variants or fragments thereof, with a variety of desired properties. For example, the invention also provides for Pvs25 and Pvs28 which have been modified in a site-specific manner to modify or delete any or all functions or epitopes. Site-specific mutations can be introduced into Pvs25 and Pvs28-encoding nucleic acid by a variety of conventional techniques, well described in the scientific and patent literature. For example, one rapid method to perform site-directed mutagenesis efficiently is the overlap extension polymerase chain reaction (OE-PCR) (Urban (1997) Nucleic Acids Res. 25:2227-2228). Other illustrative examples include: site-directed mutagenesis by overlap extension polymerase chain reaction (OE-PCR), as in Urban (1997) Nucleic Acids Res. 25:2227-2228; Ke (1997) Nucleic Acids Res 25:3371-3372, and Chattopadhyay (1997) Biotechniques 22:1054-1056, describing PCR-based site-directed mutagenesis "megaprimer" method; Bohnsack (1997) Mol. Biotechnol. 7:181-188; Ailenberg (1997) Biotechniques 22:624-626, describing site-directed mutagenesis using a PCR-based staggered re-annealing method without restriction enzymes; Nicolas (1997) Biotechniques 22:430-434, site-directed mutagenesis using long primer-unique site elimination and exonuclease III. See Gillman (1979) Gene 8:81-97; Roberts (1987) Nature 328:731-734.

In general, modifications of the sequences encoding the homologous polypeptides may be readily accomplished by a variety of well-known techniques, such as site-directed mutagenesis, described above. One of ordinary skill will appreciate that the effect of many mutations is difficult to predict. Thus, most modifications are evaluated by routine screening in a suitable assay for the desired characteristic. For instance, the effect of various modifications on the ability of the polypeptide to elicit transmission blocking can be easily determined using the mosquito feeding assays, described below. In addition, changes in the immunological character of the polypeptide can be detected by an appropriate competitive binding assay. Modifications of other properties such as redox or thermal stability, hydrophobicity, susceptibility to proteolysis, or the tendency to aggregate are all assayed according to standard techniques.

The particular procedure used to introduce the genetic material into the host cell for expression of the Pvs 25 and Pvs28 polypeptide is not particularly critical. Any of the well known procedures for introducing foreign nucleotide sequences into host cells may be used. These include the use of calcium phosphate transfection, spheroplasts, electroporation, liposomes, microinjection, plasma vectors, viral vectors and any of the other well known methods for introducing cloned genomic DNA, cDNA, synthetic DNA or other foreign genetic material into a host cell (see, e.g., Sambrook, Ausubel, supra). It is only necessary that the particular procedure utilized be capable of successfully introducing at least one gene into the host cell which is capable of expressing the gene.

The particular vector used to transport the genetic information into the cell is also not particularly critical. Any of the conventional vectors used for expression of recombinant proteins in prokaryotic and eukaryotic cells may be used.

Expression vectors for mammalian cells typically contain regulatory elements from eukaryotic viruses. SV40 vectors include pSVT7 and pMT2. Vectors derived from bovine papilloma virus include pBV-1MTHA, and vectors derived from Epstein Bar virus include pHEBO, and p2O5.

Other exemplary vectors include pMSG, pAV009/A$^+$, pMTO10/A$^+$, pMAMneo-5, bacculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The expression vector typically contains a transcription unit or expression cassette that contains all the elements required for the expression of the Pvs28 or Pvs25 polypeptide DNA in the host cells. A typical expression cassette contains a promoter operably linked to the DNA sequence encoding a Pvs28 or Pvs25 polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

The DNA sequence encoding the Pvs28 or Pvs25 polypeptide will typically be linked to a cleavable signal peptide sequence to promote secretion of the encoded protein by the transformed cell. Additional elements of the cassette may include selectable markers, enhancers and, if genomic DNA is used as the structural gene, introns with functional splice donor and acceptor sites.

Enhancer elements can stimulate transcription up to 1,000 fold from linked homologous or heterologous promoters. Enhancers are active when placed downstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, Enhancers and Eukaryotic Expression, Cold Spring Harbor Pres, Cold Spring Harbor, N.Y. 1983.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40, or a partial genomic copy of a gene already resident on the expression vector.

Pvs25 or Pvs28 coding sequences can be inserted into a host cell genome becoming an integral part of the host chromosomal DNA, using for example, retroviral vectors such as SIV or HIV, see for example, Naldini (1996) Science 272: 263-267; Vanin (1997) J. Virol. 71:7820-7826; Zufferey (1997) Nat. Biotechnol. 15:871-875, describing attenuated lentiviral vector gene delivery in vivo; Feng (1997) Nat. Biotechnol. 15:866-870, describing stable in vivo gene transduction via adenoviral/retroviral chimeric vector.

Nucleic acids of the invention can used in DNA immunization techniques. Coding sequence is operably linked to expression cassettes or vectors and injected directly as "naked" DNA into the host. The DNA can be injected intramuscularly or intradermally. See. e.g., Donnelly (1995) Ann. NY Acad. Sci. 772:40-46; Corr (1997) J. Immunol. 159: 4999-5004; Manickan (1997) J. Clin. Invest. 100:2371-2375. Variations of this technique use cationic liposome-entrapped DNA vaccines (see Gregoriadis (1997) FEBS Lett. 402:107-110); immunization with naked plasmid DNA transfected in dendritic cells (Manickan (1997) J. Leukoc. Biol. 61:125-132); and, cutaneous genetic immunization with naked DNA (Condon (1996) Nat. Med. 2:1122-1128).

Yeast expression systems, being eukaryotic, provide an attractive alternative to bacterial systems for some applications; for an overview of yeast expression systems, see. e.g., Protein Engineering Principles and Practice, eds. Cleland et al., Wiley-Liss, Inc. p 129 (1996), Barr (1988) J. Biol. Chem. 263: 16471-16478, or U.S. Pat. No. 4,546,082. A variety of yeast vectors are publicly available. For example, the expression vector pPICZ B (Invitrogen, San Diego, Calif.) has been modified to create expression vectors of the invention to express the Pvs25 or Pvs28 of the invention in yeast, such as *S. cerevisiae* and *Pichia pastoris*. Yeast episomal plasmids comprising inducible promoters can be used for the intracellular expression of the Pvs25 or Pvs28 proteins of the invention. Vectors include the pYES2 expression vector (Invitrogen, San Diego, Calif.) and pBS24.1 (Boeke (1984) Mol. Gen. Genet. 197:345); see also Jacobs (1988) Gene 67:259-269.

One embodiment uses the yeast expression vector comprising the Recombinant Protein Expression Unit called YEpRPEU-1, -2 and -3; and pIXY154 (Immunex Corp.). pIXY154 and YEpRPEU-3 have been used to express Pvs25, Pvs28 and Pvs28-Q130, a mutagenized form of Pvs28 which eliminates all, several, or, one potential N-linked glycosylation site, as discussed herein.

Yeast promoters for yeast expression vectors suitable for the expression of a Pvs25 or Pvs28 include the inducible promoter from the alcohol dehydrogenase gene, ADH2, also called the yeast alcohol dehydrogenase II gene promoter (ADH2P) (La Grange (1997) Appl. Microbiol. Biotechnol. 47:262-266). In one embodiment, the ADH2 promoter is modified to include a tract of poly A to enhance the ADH2 promoter in the expression of the polypeptides of the invention. Suitable promoters to use also include the ADH2/GAPDH hybrid promoter as described, e.g., in Cousens (1987) Gene 61:265-275.

In another embodiment, the Pvs25 or Pvs28 to be expressed can also be fused at the amino terminal end to the secretion signal sequence of the yeast mating pheromone alpha-factor (MF alpha 1S) and fused at the carboxy terminal end to the alcohol dehydrogenase II gene terminator (ADH2T), see van Rensburg (1997) J. Biotechnol. 55:43-53. The yeast alpha mating pheromone signal sequence allows for secretion of the expressed Pvs25 or Pvs28. In one embodiment, sequences are added after the KEX-2 cleavage site to enhance cleavage of the alpha factor leader; preferred embodiments include addition of the sequence EAEA (SEQ ID NO:22) and EAEAEAEAK (SEQ ID NO:23).

Yeast cell lines suitable for the present invention include e.g., BJ 2168 (Berkeley Yeast Stock Center) as well as other commonly available lines. For example, the yeast can be a *Pichia* sp., *Hansenula* sp., *Torulopsis* sp., *Saccharomyces* sp., or a *Candida* sp. The yeast can specifically be a *Pichia pastoris, Hansenula polymorpha, Torulopsis holmil, Saccharomyces fragilis, Saccharomyces cerevisiae, Saccharomyces lactis*, or a *Candida pseudotropicalis*. In other embodiments, Saccharomyces cerevisiae cell lines XV2181 from Immunex; and, 2905/6, VQ1 and VK1 which we have developed as our own yeast expression hosts.

Any of a number of other well known cells and cell lines can be used to express the polypeptides of the invention. For instance, prokaryotic cells such as *E. coli* can be used. Eukaryotic cells include, Chinese hamster ovary (CHO) cells, COS cells, mouse L cells, mouse A9 cells, baby hamster kidney cells, C127 cells, PC8 cells, and insect cells.

Following the growth of the recombinant cells and expression of the Pvs25 or Pvs28 polypeptide, the culture medium is harvested for purification of the secreted protein. The media are typically clarified by centrifugation or filtration to remove cells and cell debris and the proteins are concentrated by adsorption to any suitable resin such as, for example, CDP-Sepharose, Asialoprothrombin-Sepharose 4B, or Q Sepharose, or by use of ammonium sulfate fractionation, polyethylene glycol precipitation, or by ultrafiltration. Other routine means known in the art may be equally suitable. Further purification of the Pvs25 or Pvs28 or fusion polypeptide can be accomplished by standard techniques, for example, affinity chromatography, metal affinity chromatography (IMAC) (see, e.g., Govoroun (1997) J. Chromatogr. B. Biomed. Sci. Appl. 698:35-46; Froelich (1996) Biochem. Biophys. Res. Commun. 229:44-49), ion exchange chromatography, sizing chromatography or other protein purification techniques to obtain homogeneity, as described above. The purified proteins are then used to produce pharmaceutical compositions, as described below.

Transmission-Blocking Antibodies

A further aspect of the invention includes antibodies against Pvs25 or Pvs28 polypeptides. The antibodies are useful for diagnostic purposes or for blocking transmission of parasites. The antibodies of the invention may be polyclonal or monoclonal. Typically, polyclonal sera are preferred.

Antibodies are typically tetramers of immunoglobulin polypeptides. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains. Heavy chain types are alpha, gamma, delta, epsilon and mu. The carboxy terminal portions of immunoglobulin heavy and light chains are constant regions, while the amino terminal portions are encoded by the myriad immunoglobulin variable region genes. The variable regions of an immunoglobulin are the portions that provide antigen recognition specificity. The immunoglobulins may exist in a variety of forms including, for example, Fv, Fab, and F(ab)$_2$, as well as in single chains, e.g., Huston et al., Proc. Natl. Acad. Sci. USA, 85:5879-5883 (1988) and Bird et al., Science 242: 423-426, 1988. See, generally, Hood et al., Immunology, Benjamin, N.Y., 2nd ed. (1984), and Hunkapiller (1986) Nature, 323:15-16. Single-chain antibodies, in which genes for a heavy chain and a light chain are combined into a single coding sequence, may also be used.

Use of the Polypeptides or Nucleic Acids of the Invention to Induce Immune Responses.

The immunoglobulins, nucleic acids, and polypeptides of the present invention are also useful as prophylactics, or vaccines, for blocking transmission of malaria or other diseases caused by parasites. Compositions containing the immunoglobulins, polypeptides, nucleic acids or a cocktail thereof are administered to a subject, giving rise to an anti-Pvs25 or anti-Pvs28 polypeptide immune response in the mammal entailing the production of anti-Pvs25 or anti-Pvs28 polypeptide immunoglobulins. The Pvs25 or Pvs28 polypeptide-specific immunoglobulins then block transmission of the parasite from the subject to the arthropod vector, preventing the parasite from completing its life cycle. An amount of prophylactic composition sufficient to result in a titer of antiserum which, upon ingestion by the mosquito, is capable of blocking transmission or is capable of decreasing ability of the oocyte to mature in the mosquito (resulting in fewer infective particles passed to the mosquitoes' next target bloodmeal), is defined to be an "immunologically effective dose."

The isolated nucleic acid sequences coding for Pvs25 or Pvs28 polypeptides can be used in viruses to transfect host cells in the susceptible organism, particularly, a human. Live attenuated viruses, such as vaccinia or adenovirus, are convenient alternatives for vaccines because they are inexpensive to produce and are easily transported and administered. Vaccinia vectors and methods useful in immunization protocols are well known in the art and are described, e.g., in U.S. Pat. No. 4,722,848.

Suitable viruses for use in the present invention include, but are not limited to, pox viruses, such as, canarypox and cowpox viruses, and vaccinia viruses, alpha viruses, adenoviruses, and other animal viruses. The recombinant viruses can be produced by methods well known in the art: for example, using homologous recombination or ligating two plasmids together. A recombinant canarypox or cowpox virus can be made, for example, by inserting the gene encoding the Pvs25 or Pvs28, or other homologous polypeptide into a plasmid so that it is flanked with viral sequences on both sides. The gene is then inserted into the virus genome through homologous recombination.

A recombinant adenovirus virus can be produced, for example, by ligating two plasmids each containing 50% of the viral sequence and the DNA sequence encoding the Pvs25 or Pvs28 polypeptide. Recombinant RNA viruses such as the alpha virus can be made via a cDNA intermediate using methods known in the art.

The recombinant virus of the present invention can be used to induce anti-Pvs25 or anti-Pvs28 polypeptide antibodies in mammals, such as mice or humans. In addition, the recombinant virus can be used to produce the Pvs25 or Pvs28 polypeptides by infecting host cells which in turn express the polypeptide.

The nucleic acids can also be used to produce other recombinant microorganisms such as bacteria, yeast, and the like. For instance, BCG (Bacille Calmette Guerin) vectors are described, e.g., in Stover (1991) Nature 351:456-460. A wide variety of other vectors useful for therapeutic administration or immunization of the peptides of the invention, e.g., *Salmonella typhi, Saccharomyces* vectors and the like, will be apparent to those skilled in the art from the description herein.

The DNA encoding the polypeptides of the invention can also be administered to the patient. Typically, an expression cassette suitable for driving expression in human cells is prepared. This approach is described, for instance, in Wolff (1990) Science 247:1465-1468; U.S. Pat. Nos. 5,580,859 and 5,589,466.

The present invention also relates to host cells infected with the recombinant virus of the present invention. The host cells of the present invention are preferably eukaryotic, such as yeast cells, or mammalian, such as BSC-1 cells. Host cells infected with the recombinant virus express the Pvs25 or Pvs28 polypeptides on their cell surfaces. In addition, membrane extracts of the infected cells induce transmission blocking antibodies when used to inoculate or boost previously inoculated mammals.

In the case of vaccinia virus (e.g., strain WR), the sequence encoding the Pvs25 or Pvs28 polypeptides can be inserted into the viral genome by a number of methods including homologous recombination using a transfer vector, pTKgpt-OFIS as described in Kaslow et al., Science 252:1310-1313, 1991.

The Pvs25 or Pvs28 polypeptides or nucleic acids of the present invention can be used in pharmaceutical and vaccine compositions that are useful for administration to mammals, particularly humans, to block transmission of a variety of infectious diseases. The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., phosphate buffered saline, water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the polypeptides or nucleic acids are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, Pvs25 or Pvs28 polypeptides or nucleic acids of the invention are administered to a patient in an amount sufficient to prevent parasite development in the arthropod and thus block transmission of the disease. An amount adequate to accomplish this is defined as a "therapeutically effective dose." Amounts effective for this use will depend on, e.g., the particular polypeptide or virus, the manner of administration, the weight and general state of health of the patient, and the judgment of the prescribing physician.

The vaccines of the invention contain as an active ingredient an immunogenically effective amount of the Pvs25 or Pvs28 polypeptides, nucleic acids, or recombinant virus as described herein. Useful carriers are well known in the art, and include, e.g., thyroglobulin, albumins such as human serum albumin, tetanus toxoid, polyamino acids such as poly (D-lysine:D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

Vaccine compositions containing the polypeptides or nucleic acids of the invention are administered to a patient to elicit a transmission-blocking immune response against the antigen and thus prevent spread of the disease through the arthropod vector. Such an amount is defined as an "immunogenically effective dose." In this use, the precise amounts again depend on the patient's state of health and weight, the mode of administration, and the nature of the formulation.

As noted above, the Pvs25 or Pvs28 polypeptides of this invention may also be used to make monoclonal antibodies. Such antibodies may be useful as potential diagnostic or therapeutic agents. The polypeptides themselves may also find use as diagnostic reagents. For example, a polypeptide of the invention may be used to diagnose the presence of antibodies against *P. vivax* in a patient. Alternatively, the polypeptides can be used to determine the susceptibility of a particular individual to a particular treatment regimen, and thus may be helpful in modifying an existing treatment protocol or in determining a prognosis for an infected individual.

EXAMPLES

The following examples are offered to illustrate, but not to limit the claimed invention. Those of skill will readily recognize a variety of noncritical parameters which can be changed or modified to yield essentially similar results.

Example 1

Cloning of Pvs25

The following example details one exemplary means to isolation of a species of *Plasmodium* Pvs25. To isolate *Plas-*

*modium vivax* gene encoding Pvs25, the gene sequences of the eight known proteins-Pfs25, Pgs25, Pys25, Pbs25, Pfs28, Pgs28, Pys21 and Pbs21 were aligned and their sequence similarities analyzed, as described above.

A highly conserved nucleotide sequence in the first EGF-like domain was identified. This sequence was used to synthesize a degenerate PCR oligonucleotide. To prevent the re-amplification of Pvs28 gene, nucleotides were chosen that were not identical to the Pvs28 sequence. A sense primer (5'-GG(AT) TTT (CT)T(AG) (AG)(CT)T CA(AG) ATG AGT-3') (SEQ ID NO:6) was constructed. Using this primer with a vector-specific M13 universal primer (5'-GTA AAA CGA CGG CCA GT-3') (SEQ ID NO:7), nucleic acid sequences were amplified form a *P. vivax* genomic library (a *P. vivax* (Sal1) genomic library: Sau3AI partial digest cloned into pUC18 BamHI/BAP). The PCR reaction was: 94° C. for 10 min, then 30 cycles of 94° C. for 30 seconds, 44° C. for 60 seconds and 72° C. for 2 min 30 seconds, and finally 72° C. for 8 min.

Two different sizes of DNA fragments were amplified in this reaction. These PCR products were again amplified by using an internal degenerate primer (sense primer: 5'-TCA (AG)AT GAG T(AG)(AG) (CT)CA TTT (AGT)GA ATG-3') (SEQ ID NO:8) with a vector specific M13 universal primer (same as described above) at: 94° C. for 10 min, then 30 cycles of 94° C. for 30 seconds, 44° C. for 30 seconds and 72° C. for 1 min, and finally 72° C. for 10 min. The resultant amplified DNA was purified and cloned into pCR2.1 (Invitrogen). Using plasmid-specific sequencing primers, eight individual recombinant plasmid clones were completely sequenced (ABI PRISM 310 Genetic Analyzer; PE Applied Biosystems). This yielded a partial DNA sequence of Pvs25.

The complete nucleotide sequence for Pvs25, DNA was amplified by a nested splinkerette PCR method (see Devon (1995) Nucleic Acids Res 23: 1644-1645; Hengen (1995) Trends Biochem. Sci. 20:372-373) using pairs of gene-specific and splinkerette-specific primers. For the first PCR-sense splinkerette #1 primer: 5'-CGA ATC GTA ACC GTT CGT ACG AGA A-3' (SEQ ID NO:9); and an antisense Pvs25 specific primer: 5'-GGA CAA GCA GGA TGA TAA AG-3' (SEQ ID NO: 10). For nested PCR, sense splinkerette #2 internal primer: 5'-TCG TAC CAG AAT CGC TGT CCT CTC C-3' (SEQ ID NO:11); and an anti-sense Pvs25 specific internal primer: 5'-AGC ACA CAA GTG TCT TCC TTC-3' (SEQ ID NO:12). The template DNA was prepared by the ligation of splinkerettes with VspI digested genomic DNA obtained from *P. vivax* Sal1 strain. Primary PCR using these primers combined Hot Start (Taq Gold DNA polymerase, PE Applied Biosystems), and, Touchdown PCR to circumvent spurious priming during gene amplification (see Don (1991) Nucleic Acids Res. 19: 4008). PCR protocols were as follows: denaturation 94° C. for 10 min in the first cycle and 30 seconds thereafter; annealing, for 1 min at 60° C. initially, decreasing by 2° C. to 50° C. per cycle and 50° C. thereafter; extension, 72° C. for 2 min (cycles 1-10), then 4 min (cycles 11-20) and finally 6 min (cycles 21-30). In the primary PCR reaction 0.2 ul of ligation product was amplified in 20 ul. Secondary PCR was performed using 0.3 ul primary PCR product as a template, and the PCR condition were as follows: 94° C. for 10 min, then 10 cycles of 94° C. for 30 seconds, 50° C. for 60 second and 72° C. for 2 min, then 10 cycles of 94° C. for 30 seconds, 50° C. for 60 seconds and 72° C. for 4 min, and then 10 cycles of 94° C. for 30 seconds, 50° C. for 60 seconds and 72° C. for 6 min, and finally 72° C. for 4 min. After the nested PCR, two different sized DNA fragments were observed.

After the purification of the individual amplified DNA fragments, each DNA fragment was cloned into pCR2.1 (Invitrogen) and by using plasmid-specific sequencing primers, eight individual recombinant plasmid clones were completely sequenced (ABI PRISM 310 Genetic Analyzer; PE Applied Biosystems). The full length open reading frame of Pvs25 gene sequence (SEQ ID NO:3) was obtained from these sequences, and the polypeptide sequence (SEQ ID NO:4) encoded therein deduced (FIGS. 3 and 4, respectively).

A further pair of gene specific PCR primers was designed and constructed: the sense primer 5'-ACT TTC GTT TCA CAG CAC-3' (SEQ ID NO:13); the anti-sense primer 5'-AAA GGA CAA GCA GGA TGA TA-3' (SEQ ID NO:14). The primers were complementary (designed to hybridize) at each end of the gene sequence to amplify the full length sequence of Pvs25. By using these primers, full length Pvs25 gene was amplified from *P. vivax* Sal1 genomic library (as above). After the purification of the specific DNA fragment, we directly sequenced the DNA fragment by using Pvs25-specific sequencing primers (ABI PRISM 310 Genetic Analyzer; PE Applied Biosystems).

Analysis of the amino acid sequence deduced from the 657 base pair (bp) single ORF of Pvs25 revealed a presumptive secretory signal sequence, followed by four EGF-like domains with a total of 22 cysteines, and a short hydrophobic region at the carboxy-terminus. The sequence was not that of the Pvs28 gene; furthermore, the presence of six rather than four cysteines in the fourth EGF-like domain (a hallmark of P25 homologues rather than P28 homologues) confirmed that the sequence obtained was that of Pvs25.

Example 2

Expression of Pvs25 in Yeast

For expression in yeast, a Pvs25 DNA fragment was obtained by PCR amplification, as described above. This Pvs25 subsequence was designed to lack the presumptive secretory signal and glycosylphosphatidylinositol lipid (GPI) anchor (see, e.g., Gowda (1997) J. Biol. Chem. 272:6428-6439) sequences. A polyhistidine tag sequence was also spliced into the polypeptide coding sequence.

The resultant nucleic acid construct encoding a Pvs25 fusion protein (SEQ ID NO:16) was ligated into the NheI and ApaI restriction sites of the yeast shuttle vector, YepRPEU-3, as schematically represented in FIG. 6. Recombinant clones were electroporated into the host *S. cerevisiae* strain, VK1, and clones harboring the recombinant plasmid were screened for their ability to secrete a His6 (SEQ ID NO:24) tagged protein. A single high-producing colony was amplified in selective growth media and was used to establish a cell bank for yeast expressed Pvs25.

For these and all yeast studies described herein, fermentation procedure was essentially as described by Kaslow (1994) Biotechnology 12:494-499. A 1 ml frozen seed lot was thawed and used to inoculate 500 ml of expansion medium (8% glucose, 1% yeast nitrogen base, 2% acid-hydrolyzed casamino acids, 400 mg/L adenine sulfate, 400 mg/L uracil) in a Tunair baffled shaker flask. The cells were grown overnight at 30° C. with shaking at 250 rpm for 20-40 hr. The overnight growth in expansion medium was used to inoculate 3-3.5 L of fermentation media (0.5% glucose, 1% yeast extract, 1% yeast nitrogen base, 2% acid-hydrolyzed casamino acids, 400 mg/L adenine sulfate, 400 mg/L uracil). The Bioflo-III fermentor was set to keep pH at 5.02, temperature at 25° C. and dissolved oxygen at or above 60% by agitation between 360 and 1000 rpm. A glucose-rich nutrient medium (25% glucose, 1% yeast extract, 1% yeast nitrogen base, 2% acid-hydrolyzed casamino acids, 0.5 g/L adenine sulfate, 0.5 g/L uracil, 2.5 g/L $MgSO_4$) was fed continuously at a rate of 25 ml/hr for approximately 40 hr. 25% $NH_4OH$ was fed to keep pH at 5.02. When $OD_{600}$ of the culture reached 50 units, the carbon source was switched from glucose to 30% ethanol, 20% glycerol to induce protein secretion for 10-16 hr.

The culture supernatant was recovered by centrifugation and filter-sterilized through a 0.45 µm cellulose acetate membrane (Nalgene). The sterile medium was concentrated to 350 mLs using an Amicon tangential ultrafiltration apparatus fitted with a YD 10 spiral hollow fiber filter (Amicon), and then continuously dialyzed with 1.5 L 2× PBS pH 7.4. The retentate was incubated with Ni—NTA agarose with shaking at 4° C. overnight. After overnight incubation, the suspension was transferred to a column and the resin was washed sequentially with 2× PBS pH 7.4, 2× PBS pH 6.8 and 1× PBS pH 6.4. The protein was eluted from the resin using 0.250 M NaAcetate pH 4.5 and analyzed by SDS-PAGE. Further purification was performed by size-exclusion chromatography using a Pharmacia Superdex-75 column to which 1× PBS pH 7.4 was applied at a flow rate of 1 mL/min. One mL fractions were collected and analyzed by SDS-PAGE. Fractions containing the Pfs25 (and, in other experiment, the Pvs28, or the ~39 kD fusion protein) were pooled and protein concentration was determined by BCA (Pierce) using bovine serum albumin as the standard.

Example 3

Expression of Pvs28 in Yeast

For expression in yeast, a Pvs28 DNA fragment was obtained by PCR amplification, as described above. A polyhistidine tag sequence was spliced into the polypeptide coding sequence.

The resultant nucleic acid construct encoding a Pvs28 fusion protein (SEQ ID NO: 17) was ligated into the NheI and ApaI restriction sites of the yeast shuttle vector, YepRPEU-3 (as schematically represented in FIG. 6). Recombinant clones were electroporated into the host *S. cerevisiae* strain, VK1, and clones harboring the recombinant plasmid were screened for their ability to secrete a His6 (SEQ ID NO:24) tagged protein. High-producing colonies were amplified in selective growth media and used to establish cell banks for yeast expressed recombinant Pvs28.

Example 4

Expression of Deglycosylated Pvs28 in Yeast

For expression in yeast, a Pvs28 DNA fragment was generated, as described above. The nucleic acid was modified to encode a glutamine, rather than an asparagine, at amino acid residue number 130 (see FIG. 6, "Pvs28Q130"). A polyhistidine tag sequence was spliced into the polypeptide coding sequence.

The resultant nucleic acid construct encoding this modified (partially deglycosylated) Pvs28 fusion protein ("Pvs28Q130"; SEQ ID NO: 18) was ligated into the NheI and ApaI restriction sites of the yeast shuttle vector, YepRPEU-3 (as schematically represented in FIG. 6). Recombinant clones were electroporated into the host *S. cerevisiae* strain, VK1, and clones harboring the recombinant plasmid were screened for their ability to secrete a His6 (SEQ ID NO: 15) tagged protein. High-producing colonies were amplified in selective growth media and used to establish cell banks for yeast-expressed recombinant Pvs28.

A further variation of Pvs28 was generated (using similar techniques), as schematically represented in FIG. 6, see Pvs28NCR, and the amino acid sequence as represented by SEQ ID NO:19.

Example 5

Generation of High Titers of Antibodies Using Recombinant Pvs25, Pvs28 and Deglycosylated Pvs28 Produced in a Yeast Expression System This example demonstrates that the recombinant Pvs25 and Pvs28 of the invention, generated in the yeast expression systems, as described above, can be used to used generate high titers of antigen specific antibodies in a mammal.

Recombinant Pvs25 and Pvs28 polypeptides were generated in the yeast expression system as described above (see Examples 2 and 3, above). Immunogenic compositions comprising Pvs25 or Pvs28 and the adjuvant alum were produced by standard methodologies. Briefly, 50 micrograms (ug) of protein was absorbed by 800 ug of alum in 500 microliters (ul) of phosphate buffered saline (PBS) at pH 7.2. Purified recombinant proteins were adsorbed to alum (Superfos Biosector a/s) for 30 min at room temperature with continuous rocking. The suspensions were then stored at 4° C. until used to vaccinate mice by the intraperitoneal route.

Mice of various inbred strains, listed in FIG. 7 (which also schematically summarizes and illustrates the immunization protocol) were used. Each was prebled before injection antigen (or alum control). The animals were then immunized intraperitoneally (IP) with either the recombinant Pvs25-containing or Pvs28-containing immunogenic compositions; or alum alone. The mice were boosted with similar compositions and dosages at day 21 and day 42. All mice were bled at day 56. Harvested blood was prepared by standard protocols, and the test bleeds and pre-bleed controls were analyzed for anti-Pfs25 and Pvs28 antibody titers using various standard immunological techniques, as described above.

The antibody titer data clearly demonstrated high titers of anti-Pfs25 antiserum were generated in all five strains of mice; the alum only test bleeds showed no anti-Pvs25 reactivity above background. Data also clearly demonstrated that high titers of anti-Pfs28 antiserum were generated in all four or the five strains of mice (only the C57BL/6 strain did not respond to the Pvs28-containing immunogenic composition); the alum only test bleeds showed no anti-Pvs25 reactivity above background.

Example 6

Anti-Pvs Antiserum have *P. vivax* Transmission Blocking Activity

Transmission-blocking activity was assayed as described previously Quakyi (1987) J. Immunol. 139: 4213-4217. Briefly, test sera were mixed with mature in vitro-cultured *P. vivax* gametocytes and fed to mosquitoes through an artificial membrane stretched across the base of a water-jacketed glass cylinder. The parasites in the blood meal were allowed to develop in the mosquito to the easily identifiable oocyst stage by maintaining the mosquitoes in a secured insectary for 6-8 days. Infectivity was measured by dissecting the midgut, staining it with mercurochrome, and then counting the number of oocysts per mosquito midgut of approximately 20 mosquitoes. The data was analyzed as described in Kaslow et al Vaccine Res. 2:95-103.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A composition comprising an isolated Pvs25 polypeptide having at least 95% amino acid sequence identity to SEQ ID NO:4, wherein the Pvs25 polypeptide induces production of antibodies in a susceptible mammal against a 25 kD protein on the surface of *Plasmodium vivax* zygotes and ookinetes, wherein the antibodies against the 25 kD protein block the transmission of *P. vivax* from a mosquito.

2. The composition of claim 1, wherein the Pvs25 polypeptide is encoded by a nucleic acid sequence having at least 95% sequence identity to SEQ ID NO:3.

3. The composition of claim 1, wherein the Pvs25 polypeptide has an amino acid sequence as shown in SEQ ID NO:4.

4. The composition of claim 1, wherein the composition further comprises a Pvs28 polypeptide having at least 95% sequence identity to SEQ ID NO:2, wherein the Pvs28 polypeptide induces production of antibodies in a susceptible mammal against a 28 kD protein on the surface of *Plasmodium vivax* zygotes and ookinetes, wherein the antibodies against the 28 kD protein block the transmission of *P. vivax* from a mosquito.

5. The composition of claim 1, further comprising a pharmaceutically acceptable carrier.

6. The composition of claim 5, wherein the Pvs25 polypeptide comprises an amino acid having the sequence as set forth in SEQ ID NO:4.

7. The composition of claim 5, wherein the composition further comprises a Pvs28 polypeptide having at least 95% sequence identity to SEQ ID NO:2, wherein the Pvs28 polypeptide induces production of antibodies in a susceptible mammal against a 28 kD protein on the surface of *Plasmodium vivax* zygotes and ookinetes, wherein the antibodies against the 28 kD protein block the transmission of *P. vivax* from a mosquito.

8. A method of inducing antibody production against Pvs25 on the surface of *Plasmodium vivax* ookinetes, the method comprising administering to a susceptible mammal a pharmaceutical composition comprising a Pvs25 polypeptide having at least 95% amino acid sequence identity to SEQ ID NO:4 in an amount sufficient to induce production of antibodies in the mammal against a 25 kD protein on the surface of *Plasmodium vivax* zygotes and ookinetes, wherein the antibodies against the 25 kD protein block the transmission of *P. vivax* from a mosquito.

9. The method of claim 8, wherein the Pvs25 polypeptide in the pharmaceutical composition is recombinantly produced.

10. The method of claim 8, wherein the susceptible mammal is a human.

11. The method of claim 8, wherein the Pvs25 polypeptide in the pharmaceutical composition is on the surface of a recombinant virus.

12. The method of claim 8, wherein the Pvs25 polypeptide is encoded by a nucleic acid having at least 95% nucleic acid sequence identity to SEQ ID NO:3.

13. The method of claim 12, wherein the Pvs25 polypeptide comprises an amino acid having the sequence as set forth in SEQ ID NO:4.

14. The method of claim 8, further comprising administering a Pvs28 polypeptide having at least 95% amino acid sequence identity to SEQ ID NO:2, wherein the Pvs28 polypeptide induces production of antibodies in a susceptible mammal against a 28 kD protein on the surface of *Plasmodium vivax* zygotes and ookinetes, wherein the antibodies against the 28 kD protein block the transmission of *P. vivax* from a mosquito.

15. The method of claim 8, wherein the Pvs25 polypeptide is administered intramuscularly, intradermally, subcutaneously, or intranasally.

16. The method of claim 14, wherein the Pvs25 polypeptide and the Pvs28 polypeptide are administered as a fusion protein having at least 95% amino acid sequence identity to SEQ ID NO:5.

17. The composition of claim 4, wherein the Pvs25 polypeptide and the Pvs28 polypeptide are a fusion protein having at least 95% amino acid sequence identity to SEQ ID NO:5.

* * * * *

SEQUENCE LISTING

```
<160> NUMBER OF SEQ ID NOS: 24

<210> SEQ ID NO 1
<211> LENGTH: 1066
<212> TYPE: DNA
<213> ORGANISM: Plasmodium vivax
<220> FEATURE:
<221> NAME/KEY: CDS
<222> LOCATION: (147)..(857)
<223> OTHER INFORMATION: Pvs28

<400> SEQUENCE: 1
tccactcctc tcttgttcca cactttatct ttgtttcccc ccattcggcc accaactgca    60
ttatacaaaa acgactcccc ctttgagata acacccaact gagctcgatt ccccctcccc   120 actttttgcgc ctccccttg ttcaaa atg aat acc tac cac agc ttg ctg ttc   173
                                Met Asn Thr Tyr His Ser Leu Leu Phe
                                  1               5 ctt ctg gcc atc gtg ctt act gtt aag cac acc ttc gca aag gtc acc   221
Leu Leu Ala Ile Val Leu Thr Val Lys His Thr Phe Ala Lys Val Thr
 10              15                  20                  25 gcg gag acc caa tgc aaa aat ggc tat gta gtc caa atg agc aat cat   269
Ala Glu Thr Gln Cys Lys Asn Gly Tyr Val Val Gln Met Ser Asn His
                 30                  35                  40 ttt gaa tgc aaa tgc aac gac ggg ttt gtt atg gca aat gaa aac act   317
Phe Glu Cys Lys Cys Asn Asp Gly Phe Val Met Ala Asn Glu Asn Thr
             45                  50                  55 tgc gag gaa aaa cgc gat tgc aca aat cca caa aat gta aat aaa aac   365
Cys Glu Glu Lys Arg Asp Cys Thr Asn Pro Gln Asn Val Asn Lys Asn
         60                  65                  70 tgt gga gac tac gct gtg tgt gca aac acc aga atg aat gat gag gaa   413
Cys Gly Asp Tyr Ala Val Cys Ala Asn Thr Arg Met Asn Asp Glu Glu
     75                  80                  85 aga gca tta cga tgc ggc tgc ata tta ggg tac acc gta atg aat gag   461
Arg Ala Leu Arg Cys Gly Cys Ile Leu Gly Tyr Thr Val Met Asn Glu
 90                  95                 100                 105 gtg tgt act cca aat aaa tgt aac ggc gtt ttg tgt gga aag gga aag   509
Val Cys Thr Pro Asn Lys Cys Asn Gly Val Leu Cys Gly Lys Gly Lys
                110                 115                 120 tgc atc tta gat ccc gct aat gtg aac agc acc atg tgc tct tgt aat   557
Cys Ile Leu Asp Pro Ala Asn Val Asn Ser Thr Met Cys Ser Cys Asn
            125                 130                 135 ata gga acc aca ttg gat gaa tct aaa aaa tgt gga aag cca gga aaa   605
Ile Gly Thr Thr Leu Asp Glu Ser Lys Lys Cys Gly Lys Pro Gly Lys
        140                 145                 150 act gaa tgc acg ttg aag tgt aag gca aac gaa gaa tgt aaa gag act   653
Thr Glu Cys Thr Leu Lys Cys Lys Ala Asn Glu Glu Cys Lys Glu Thr
    155                 160                 165 cag aat tat tac aag tgc gtt gcg aag gga agc ggc gga gaa ggc agc   701
Gln Asn Tyr Tyr Lys Cys Val Ala Lys Gly Ser Gly Gly Glu Gly Ser
170                 175                 180                 185 ggt gga gaa ggc agc ggc gga gag ggc agc gga gag ggc agc ggc       749
Gly Gly Glu Gly Ser Gly Gly Glu Gly Ser Gly Gly Glu Gly Ser Gly
```

```
                    190                 195                 200
gga gag ggc agc ggt gga gac aca gga gca gct tac agt ctc atg aac    797
Gly Glu Gly Ser Gly Gly Asp Thr Gly Ala Ala Tyr Ser Leu Met Asn
            205                 210                 215 gga tct gca gta atc agc ata cta ctt gta ttc gcc ttc ttc atg atg    845
Gly Ser Ala Val Ile Ser Ile Leu Leu Val Phe Ala Phe Phe Met Met
            220                 225                 230 tca tta gtg tagacgattc tacacacaca cacaaacata cacaagggga            894
Ser Leu Val
        235 gaagcgtctc acagagtcag ttcaagtcat acgcacaaaa aaggaaagta catccagctg  954 gtgaaagagc atttatgtgt gcagttatcc ttgggagaag caccctccac ccagttgcgt 1014 tgctgttacc ttaaaactta gtggcaccca tatcgaattt gactttgctc gc         1066

<210> SEQ ID NO 2
<211> LENGTH: 236
<212> TYPE: PRT
<213> ORGANISM: Plasmodium vivax

<400> SEQUENCE: 2

Met Asn Thr Tyr His Ser Leu Leu Phe Leu Leu Ala Ile Val Leu Thr
 1               5                  10                  15

Val Lys His Thr Phe Ala Lys Val Thr Ala Glu Thr Gln Cys Lys Asn
            20                  25                  30

Gly Tyr Val Val Gln Met Ser Asn His Phe Glu Cys Lys Cys Asn Asp
        35                  40                  45

Gly Phe Val Met Ala Asn Glu Asn Thr Cys Glu Glu Lys Arg Asp Cys
    50                  55                  60

Thr Asn Pro Gln Asn Val Asn Lys Asn Cys Gly Asp Tyr Ala Val Cys
65                  70                  75                  80

Ala Asn Thr Arg Met Asn Asp Glu Glu Arg Ala Leu Arg Cys Gly Cys
                85                  90                  95

Ile Leu Gly Tyr Thr Val Met Asn Glu Val Cys Thr Pro Asn Lys Cys
            100                 105                 110

Asn Gly Val Leu Cys Gly Lys Gly Lys Cys Ile Leu Asp Pro Ala Asn
        115                 120                 125

Val Asn Ser Thr Met Cys Ser Cys Asn Ile Gly Thr Thr Leu Asp Glu
    130                 135                 140

Ser Lys Lys Cys Gly Lys Pro Gly Lys Thr Glu Cys Thr Leu Lys Cys
145                 150                 155                 160

Lys Ala Asn Glu Glu Cys Lys Glu Thr Gln Asn Tyr Tyr Lys Cys Val
                165                 170                 175

Ala Lys Gly Ser Gly Gly Glu Gly Ser Gly Gly Glu Gly Ser Gly Gly
            180                 185                 190

Glu Gly Ser Gly Gly Glu Gly Ser Gly Gly Glu Gly Ser Gly Gly Asp
        195                 200                 205

Thr Gly Ala Ala Tyr Ser Leu Met Asn Gly Ser Ala Val Ile Ser Ile
    210                 215                 220

Leu Leu Val Phe Ala Phe Phe Met Met Ser Leu Val
225                 230                 235

<210> SEQ ID NO 3
<211> LENGTH: 995
<212> TYPE: DNA
<213> ORGANISM: Plasmodium vivax
<220> FEATURE:
```

<220> NAME/KEY: CDS
<222> LOCATION: (255)..(914)
<223> OTHER INFORMATION: Pvs25

<400> SEQUENCE: 3

```
ctgactttcg tttcacagca ctgatttttt tgttcgaccg ctcaattcgc cacttgccat      60
tttcgattgt ttgcttgttt gcttttttgc ttattcgccc gttttccgc ttgcccgttc      120 gcccgctcca caacgcgccg ctgcaaaggt tgcccaccac cgaccacaaa aactattca      180 ccaccatccg agcggaaagg aacgccgccc actgtgctgc ctacctcccc gaataacaac      240
tccacttagc caaa atg aac tcc tac tac agc ctc ttc gtt ttt ttc ctc       290
              Met Asn Ser Tyr Tyr Ser Leu Phe Val Phe Phe Leu
              1               5                   10 gtc caa att gcg cta aag tat agc aag gca gcc gtc acg gta gac acc       338
Val Gln Ile Ala Leu Lys Tyr Ser Lys Ala Ala Val Thr Val Asp Thr
        15                  20                  25 ata tgc aaa aat gga cag ctg gtt caa atg agt aac cac ttt aag tgt       386
Ile Cys Lys Asn Gly Gln Leu Val Gln Met Ser Asn His Phe Lys Cys
    30                  35                  40 atg tgt aac gaa ggg ctg gtg cac ctt tcc gaa aat aca tgt gaa gaa       434
Met Cys Asn Glu Gly Leu Val His Leu Ser Glu Asn Thr Cys Glu Glu
45                  50                  55                  60 aaa aat gaa tgc aag aaa gaa acc cta ggc aaa gca tgc ggg gaa ttt       482
Lys Asn Glu Cys Lys Lys Glu Thr Leu Gly Lys Ala Cys Gly Glu Phe
                65                  70                  75 ggc cag tgt ata gaa aac cca gac cca gca cag gta aac atg tac aaa       530
Gly Gln Cys Ile Glu Asn Pro Asp Pro Ala Gln Val Asn Met Tyr Lys
            80                  85                  90 tgt ggt tgc att gag ggc tac act ttg aag gaa gac act tgt gtg ctt       578
Cys Gly Cys Ile Glu Gly Tyr Thr Leu Lys Glu Asp Thr Cys Val Leu
        95                  100                 105 gat gta tgt caa tac aaa aat tgt gga gaa agt ggc gaa tgc att gtt       626
Asp Val Cys Gln Tyr Lys Asn Cys Gly Glu Ser Gly Glu Cys Ile Val
    110                 115                 120 gag tac ctc tcg gaa atc caa agt gca ggt tgc tca tgt gct att ggc       674
Glu Tyr Leu Ser Glu Ile Gln Ser Ala Gly Cys Ser Cys Ala Ile Gly
125                 130                 135                 140 aaa gtc ccc aat cca gaa gat gag aaa aaa tgt acc aaa acg gga gaa       722
Lys Val Pro Asn Pro Glu Asp Glu Lys Lys Cys Thr Lys Thr Gly Glu
                145                 150                 155 act gct tgt caa ttg aaa tgt aac aca gat aat gaa gtc tgc aaa aat       770
Thr Ala Cys Gln Leu Lys Cys Asn Thr Asp Asn Glu Val Cys Lys Asn
            160                 165                 170 gtt gaa gga gtt tac aag tgc cag tgt atg gaa ggc ttt acg ttc gac       818
Val Glu Gly Val Tyr Lys Cys Gln Cys Met Glu Gly Phe Thr Phe Asp
        175                 180                 185 aaa gag aaa aat gta tgc ctt tcc tat tct gta ttt aac atc cta aac       866
Lys Glu Lys Asn Val Cys Leu Ser Tyr Ser Val Phe Asn Ile Leu Asn
    190                 195                 200 tac tcc ctc ttc ttt atc atc ctg ctt gtc ctt tcg tac gtc ata           911
Tyr Ser Leu Phe Phe Ile Ile Leu Leu Val Leu Ser Tyr Val Ile
205                 210                 215 taagtgcgaa acttgcgcag ctaagcagcg caaattttt aagttaaaat acttttcttt      971
actgaactta ccgacttgtg atgt                                            995
```

<210> SEQ ID NO 4
<211> LENGTH: 219
<212> TYPE: PRT
<213> ORGANISM: Plasmodium vivax

<400> SEQUENCE: 4

```
Met Asn Ser Tyr Tyr Ser Leu Phe Val Phe Leu Val Gln Ile Ala
 1               5                  10                  15

Leu Lys Tyr Ser Lys Ala Ala Val Thr Val Asp Thr Ile Cys Lys Asn
            20                  25                  30

Gly Gln Leu Val Gln Met Ser Asn His Phe Lys Cys Met Cys Asn Glu
        35                  40                  45

Gly Leu Val His Leu Ser Glu Asn Thr Cys Glu Glu Lys Asn Glu Cys
    50                  55                  60

Lys Lys Glu Thr Leu Gly Lys Ala Cys Gly Glu Phe Gly Gln Cys Ile
65                  70                  75                  80

Glu Asn Pro Asp Pro Ala Gln Val Asn Met Tyr Lys Cys Gly Cys Ile
                85                  90                  95

Glu Gly Tyr Thr Leu Lys Glu Asp Thr Cys Val Leu Asp Val Cys Gln
            100                 105                 110

Tyr Lys Asn Cys Gly Glu Ser Gly Glu Cys Ile Val Glu Tyr Leu Ser
        115                 120                 125

Glu Ile Gln Ser Ala Gly Cys Ser Cys Ala Ile Gly Lys Val Pro Asn
    130                 135                 140

Pro Glu Asp Glu Lys Lys Cys Thr Lys Thr Gly Glu Thr Ala Cys Gln
145                 150                 155                 160

Leu Lys Cys Asn Thr Asp Asn Glu Val Cys Lys Asn Val Glu Gly Val
                165                 170                 175

Tyr Lys Cys Gln Cys Met Glu Gly Phe Thr Phe Asp Lys Glu Lys Asn
            180                 185                 190

Val Cys Leu Ser Tyr Ser Val Phe Asn Ile Leu Asn Tyr Ser Leu Phe
        195                 200                 205

Phe Ile Ile Leu Leu Val Leu Ser Tyr Val Ile
    210                 215
```

<210> SEQ ID NO 5
<211> LENGTH: 377
<212> TYPE: PRT
<213> ORGANISM: Artificial Sequence
<220> FEATURE:
<223> OTHER INFORMATION: Description of Artificial Sequence:Pvs25-Pvs28
    fusion protein

<400> SEQUENCE: 5

```
Ala Val Thr Val Asp Thr Ile Cys Lys Asn Gly Gln Leu Val Gln Met
 1               5                  10                  15

Ser Asn His Phe Lys Cys Met Cys Asn Glu Gly Leu Val His Leu Ser
            20                  25                  30

Glu Asn Thr Cys Glu Glu Lys Asn Glu Cys Lys Lys Glu Thr Leu Gly
        35                  40                  45

Lys Ala Cys Gly Glu Phe Gly Gln Cys Ile Glu Asn Pro Asp Pro Ala
    50                  55                  60

Gln Val Asn Met Tyr Lys Cys Gly Cys Ile Glu Gly Tyr Thr Leu Lys
65                  70                  75                  80

Glu Asp Thr Cys Val Leu Asp Val Cys Gln Tyr Lys Asn Cys Gly Glu
                85                  90                  95

Ser Gly Glu Cys Ile Val Glu Tyr Leu Ser Glu Ile Gln Ser Ala Gly
            100                 105                 110

Cys Ser Cys Ala Ile Gly Lys Val Pro Asn Pro Glu Asp Glu Lys Lys
        115                 120                 125
```

```
Cys Thr Lys Thr Gly Glu Thr Ala Cys Gln Leu Lys Cys Asn Thr Asp
    130                 135                 140
Asn Glu Val Cys Lys Asn Val Glu Gly Val Tyr Lys Cys Gln Cys Met
145                 150                 155                 160
Glu Gly Phe Thr Phe Asp Lys Glu Lys Asn Val Cys Leu Ser Gly Gly
                165                 170                 175
Gly Pro Gly Gly Gly Ala Lys Val Thr Ala Glu Thr Gln Cys Lys Asn
            180                 185                 190
Gly Tyr Val Val Gln Met Ser Asn His Phe Glu Cys Lys Cys Asn Asp
        195                 200                 205
Gly Phe Val Met Ala Asn Glu Asn Thr Cys Glu Glu Lys Arg Asp Cys
    210                 215                 220
Thr Asn Pro Gln Asn Val Asn Lys Asn Cys Gly Asp Tyr Ala Val Cys
225                 230                 235                 240
Ala Asn Thr Arg Met Asn Asp Glu Glu Arg Ala Leu Arg Cys Gly Cys
                245                 250                 255
Ile Leu Gly Tyr Thr Val Met Asn Glu Val Cys Thr Pro Asn Lys Cys
            260                 265                 270
Asn Gly Val Leu Cys Gly Lys Gly Lys Cys Ile Leu Asp Pro Ala Asn
        275                 280                 285
Val Asn Ser Thr Met Cys Ser Cys Asn Ile Gly Thr Thr Leu Asp Glu
    290                 295                 300
Ser Lys Lys Cys Gly Lys Pro Gly Lys Thr Glu Cys Thr Leu Lys Cys
305                 310                 315                 320
Lys Ala Asn Glu Glu Cys Lys Glu Thr Gln Asn Tyr Tyr Lys Cys Val
                325                 330                 335
Ala Lys Gly Ser Gly Gly Glu Gly Ser Gly Gly Glu Gly Ser Gly Gly
            340                 345                 350
Glu Gly Ser Gly Gly Glu Gly Ser Gly Gly Glu Gly Ser Gly Gly Asp
        355                 360                 365
Thr Gly Ala Ala Tyr Ser Leu Met Asn
    370                 375

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:sense primer

<400> SEQUENCE: 6
ggwtttytrr ytcaratgag t                                              21

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:vector-
      specific M13 universal primer

<400> SEQUENCE: 7
gtaaaacgac ggccagt                                                   17

<210> SEQ ID NO 8
<211> LENGTH: 24
<212> TYPE: DNA
<213> ORGANISM: Artificial Sequence
```

<220> FEATURE:
<223> OTHER INFORMATION: Description of Artificial Sequence:internal
    degenerate sense primer

<400> SEQUENCE: 8
tcaratgagt rrycatttdg aatg                                          24

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:PCR-sense
    splinkerette #1 primer

<400> SEQUENCE: 9
cgaatcgtaa ccgttcgtac gagaa                                         25

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:antisense
    Pvs25 specific primer

<400> SEQUENCE: 10
ggacaagcag gatgataaag                                               20

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:nested PCR
    sense splinkerette #2 internal primer

<400> SEQUENCE: 11
tcgtaccaga atcgctgtcc tctcc                                         25

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:anti-sense
    Pvs25 specific internal primer

<400> SEQUENCE: 12
agcacacaag tgtcttcctt c                                             21

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:gene
    specific PCR sense primer

<400> SEQUENCE: 13
actttcgttt cacagcac                                                 18

<210> SEQ ID NO 14
<211> LENGTH: 20
<212> TYPE: DNA
<213> ORGANISM: Artificial Sequence
<220> FEATURE:

<223> OTHER INFORMATION: Description of Artificial Sequence:gene
       specific PCR anti-sense primer

<400> SEQUENCE: 14
aaaggacaag caggatgata                                             20

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:flexible
       linker

<400> SEQUENCE: 15

Gly Gly Gly Pro Gly Gly Gly
  1               5

<210> SEQ ID NO 16
<211> LENGTH: 186
<212> TYPE: PRT
<213> ORGANISM: Artificial Sequence
<220> FEATURE:
<223> OTHER INFORMATION: Description of Artificial Sequence:Pvs25 fusion
       protein

<400> SEQUENCE: 16

Glu Ala Glu Ala Ser Ala Val Thr Val Asp Thr Ile Cys Lys Asn Gly
  1               5                  10                  15

Gln Leu Val Gln Met Ser Asn His Phe Lys Cys Met Cys Asn Glu Gly
             20                  25                  30

Leu Val His Leu Ser Glu Asn Thr Cys Glu Glu Lys Asn Glu Cys Lys
         35                  40                  45

Lys Glu Thr Leu Gly Lys Ala Cys Gly Glu Phe Gly Gln Cys Ile Glu
     50                  55                  60

Asn Pro Asp Pro Ala Gln Val Asn Met Tyr Lys Cys Gly Cys Ile Glu
 65                  70                  75                  80

Gly Tyr Thr Leu Lys Glu Asp Thr Cys Val Leu Asp Val Cys Gln Tyr
                 85                  90                  95

Lys Asn Cys Gly Glu Ser Gly Glu Cys Ile Val Glu Tyr Leu Ser Glu
            100                 105                 110

Ile Gln Ser Ala Gly Cys Ser Cys Ala Ile Gly Lys Val Pro Glu Pro
        115                 120                 125

Glu Asp Glu Lys Lys Cys Thr Lys Thr Gly Glu Thr Ala Cys Gln Leu
    130                 135                 140

Lys Cys Asn Thr Asp Asn Glu Val Cys Lys Asn Val Glu Gly Val Tyr
145                 150                 155                 160

Lys Cys Gln Cys Met Glu Gly Phe Thr Phe Cys Lys Glu Lys Asn Val
                165                 170                 175

Cys Leu Gly Pro His His His His His His
            180                 185

<210> SEQ ID NO 17
<211> LENGTH: 205
<212> TYPE: PRT
<213> ORGANISM: Artificial Sequence
<220> FEATURE:
<223> OTHER INFORMATION: Description of Artificial Sequence:Pvs28 fusion
       protein

<400> SEQUENCE: 17

Glu Ala Glu Ala Ser Lys Val Thr Ala Glu Thr Gln Cys Lys Asn Gly
1               5                   10                  15

Tyr Val Val Gln Met Ser Asn His Phe Glu Cys Lys Cys Asn Asp Gly
                20                  25                  30

Phe Val Leu Ala Asn Glu Asn Thr Cys Glu Glu Lys Arg Asp Cys Thr
            35                  40                  45

Asn Pro Gln Asn Val Asn Lys Asn Cys Gly Asp Tyr Ala Val Cys Ala
        50                  55                  60

Asn Thr Arg Met Asn Asn Glu Glu Arg Ala Leu Arg Cys Gly Cys Ile
65                  70                  75                  80

Leu Gly Tyr Thr Val Met Asn Glu Val Cys Thr Pro Tyr Lys Cys Asn
                85                  90                  95

Gly Val Leu Cys Gly Lys Gly Lys Cys Ile Leu Asp Pro Ala Asn Val
            100                 105                 110

Asn Ser Thr Met Cys Ser Cys Asn Ile Gly Ser Thr Leu Asp Glu Ser
        115                 120                 125

Lys Lys Cys Gly Lys Pro Gly Lys Thr Glu Cys Thr Leu Lys Cys Lys
130                 135                 140

Ala Asn Glu Glu Cys Lys Glu Thr Gln Asn Tyr Tyr Lys Cys Val Ala
145                 150                 155                 160

Lys Gly Ser Gly Gly Glu Gly Ser Gly Gly Glu Gly Ser Gly Gly Glu
                165                 170                 175

Gly Ser Gly Gly Glu Gly Ser Gly Gly Glu Gly Ser Gly Gly Asp Thr
            180                 185                 190

Gly Ala Ala Tyr Ser Gly Pro His His His His His
            195                 200                 205

<210> SEQ ID NO 18
<211> LENGTH: 205
<212> TYPE: PRT
<213> ORGANISM: Artificial Sequence
<220> FEATURE:
<223> OTHER INFORMATION: Description of Artificial Sequence:Pvs28Q130
      fusion protein

<400> SEQUENCE: 18

Glu Ala Glu Ala Ser Lys Val Thr Ala Glu Thr Gln Cys Lys Asn Gly
1               5                   10                  15

Tyr Val Val Gln Met Ser Asn His Phe Glu Cys Lys Cys Asn Asp Gly
                20                  25                  30

Phe Val Leu Ala Asn Glu Asn Thr Cys Glu Glu Lys Arg Asp Cys Thr
            35                  40                  45

Asn Pro Gln Asn Val Asn Lys Asn Cys Gly Asp Tyr Ala Val Cys Ala
        50                  55                  60

Asn Thr Arg Met Asn Asn Glu Glu Arg Ala Leu Arg Cys Gly Cys Ile
65                  70                  75                  80

Leu Gly Tyr Thr Val Met Asn Glu Val Cys Thr Pro Tyr Lys Cys Asn
                85                  90                  95

Gly Val Leu Cys Gly Lys Gly Lys Cys Ile Leu Asp Pro Ala Asn Val
            100                 105                 110

Gln Ser Thr Met Cys Ser Cys Asn Ile Gly Ser Thr Leu Asp Glu Ser
        115                 120                 125

Lys Lys Cys Gly Lys Pro Gly Lys Thr Glu Cys Thr Leu Lys Cys Lys
130                 135                 140

Ala Asn Glu Glu Cys Lys Glu Thr Gln Asn Tyr Tyr Lys Cys Val Ala
145                 150                 155                 160

-continued

Lys Gly Ser Gly Gly Glu Gly Ser Gly Gly Glu Gly Ser Gly Gly Glu
              165                 170                 175

Gly Ser Gly Gly Glu Gly Ser Gly Gly Glu Gly Ser Gly Gly Asp Thr
              180                 185                 190

Gly Ala Ala Tyr Ser Gly Pro His His His His His
              195                 200             205

<210> SEQ ID NO 19
<211> LENGTH: 169
<212> TYPE: PRT
<213> ORGANISM: Artificial Sequence
<220> FEATURE:
<223> OTHER INFORMATION: Description of Artificial Sequence:Pvs28NCR
      fusion protein

<400> SEQUENCE: 19

Glu Ala Glu Ala Ser Lys Val Thr Ala Glu Thr Gln Cys Lys Asn Gly
  1               5                  10                  15

Tyr Val Val Gln Met Ser Asn His Phe Glu Cys Lys Cys Asn Asp Gly
                 20                  25                  30

Phe Val Leu Ala Asn Glu Asn Thr Cys Glu Glu Lys Arg Asp Cys Thr
             35                  40                  45

Asn Pro Gln Asn Val Asn Lys Asn Cys Gly Asp Tyr Ala Val Cys Ala
         50                  55                  60

Asn Thr Arg Met Asn Asn Glu Glu Arg Ala Leu Arg Cys Gly Cys Ile
 65                  70                  75                  80

Leu Gly Tyr Thr Val Met Asn Glu Val Cys Thr Pro Tyr Lys Cys Asn
                 85                  90                  95

Gly Val Leu Cys Gly Lys Gly Lys Cys Ile Leu Asp Pro Ala Asn Val
                100                 105                 110

Asn Ser Thr Met Cys Ser Cys Asn Ile Gly Ser Thr Leu Asp Glu Ser
             115                 120                 125

Lys Lys Cys Gly Lys Pro Gly Lys Thr Glu Cys Thr Leu Lys Cys Lys
         130                 135                 140

Ala Asn Glu Glu Cys Lys Glu Thr Gln Asn Tyr Tyr Lys Cys Val Ala
145                 150                 155                 160

Lys Gly Pro His His His His His His
                165

<210> SEQ ID NO 20
<211> LENGTH: 174
<212> TYPE: PRT
<213> ORGANISM: Artificial Sequence
<220> FEATURE:
<223> OTHER INFORMATION: Description of Artificial Sequence:Pvs25 domain
      of Pvs25-Pvs28 fusion protein

<400> SEQUENCE: 20

Ala Val Thr Val Asp Thr Ile Cys Lys Asn Gly Gln Leu Val Gln Met
  1               5                  10                  15

Ser Asn His Phe Lys Cys Met Cys Asn Glu Gly Leu Val His Leu Ser
                 20                  25                  30

Glu Asn Thr Cys Glu Glu Lys Asn Glu Cys Lys Lys Glu Thr Leu Gly
             35                  40                  45

Lys Ala Cys Gly Glu Phe Gly Gln Cys Ile Glu Asn Pro Asp Pro Ala
         50                  55                  60

Gln Val Asn Met Tyr Lys Cys Gly Cys Ile Glu Gly Tyr Thr Leu Lys
 65                  70                  75                  80

```
Glu Asp Thr Cys Val Leu Asp Val Cys Gln Tyr Lys Asn Cys Gly Glu
                85                  90                  95

Ser Gly Glu Cys Ile Val Glu Tyr Leu Ser Glu Ile Gln Ser Ala Gly
            100                 105                 110

Cys Ser Cys Ala Ile Gly Lys Val Pro Asn Pro Asp Glu Lys Lys
        115                 120                 125

Cys Thr Lys Thr Gly Glu Thr Ala Cys Gln Leu Lys Cys Asn Thr Asp
        130                 135                 140

Asn Glu Val Cys Lys Asn Val Glu Gly Val Tyr Lys Cys Gln Cys Met
145                 150                 155                 160

Glu Gly Phe Thr Phe Asp Lys Glu Lys Asn Val Cys Leu Ser
                165                 170
```

<210> SEQ ID NO 21
<211> LENGTH: 196
<212> TYPE: PRT
<213> ORGANISM: Artificial Sequence
<220> FEATURE:
<223> OTHER INFORMATION: Description of Artificial Sequence:Pvs28 domain
      of Pvs25-Pvs28 fusion protein

<400> SEQUENCE: 21

```
Ala Lys Val Thr Ala Glu Thr Gln Cys Lys Asn Gly Tyr Val Val Gln
 1               5                  10                  15

Met Ser Asn His Phe Glu Cys Lys Cys Asn Asp Gly Phe Val Met Ala
            20                  25                  30

Asn Glu Asn Thr Cys Glu Glu Lys Arg Asp Cys Thr Asn Pro Gln Asn
        35                  40                  45

Val Asn Lys Asn Cys Gly Asp Tyr Ala Val Cys Ala Asn Thr Arg Met
    50                  55                  60

Asn Asp Glu Glu Arg Ala Leu Arg Cys Gly Cys Ile Leu Gly Tyr Thr
65                  70                  75                  80

Val Met Asn Glu Val Cys Thr Pro Asn Lys Cys Asn Gly Val Leu Cys
                85                  90                  95

Gly Lys Gly Lys Cys Ile Leu Asp Pro Ala Asn Val Asn Ser Thr Met
            100                 105                 110

Cys Ser Cys Asn Ile Gly Thr Thr Leu Asp Glu Ser Lys Lys Cys Gly
        115                 120                 125

Lys Pro Gly Lys Thr Glu Cys Thr Leu Lys Cys Lys Ala Asn Glu Glu
    130                 135                 140

Cys Lys Glu Thr Gln Asn Tyr Tyr Lys Cys Val Ala Lys Gly Ser Gly
145                 150                 155                 160

Gly Glu Gly Ser Gly Gly Glu Gly Ser Gly Gly Glu Gly Ser Gly Gly
                165                 170                 175

Glu Gly Ser Gly Gly Glu Gly Ser Gly Gly Asp Thr Gly Ala Ala Tyr
            180                 185                 190

Ser Leu Met Asn
        195
```

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:sequence
      added to enhance cleavage of alpha factor leader

<400> SEQUENCE: 22

```
Glu Ala Glu Ala
  1

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:sequence
      added to enhance cleavage of alpha factor leader

<400> SEQUENCE: 23

Glu Ala Glu Ala Glu Ala Glu Ala Lys
  1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:
      polyhistidine tag

<400> SEQUENCE: 24

His His His His His His
  1               5
```